United States Patent [19]

Chibata et al.

[11] 4,138,292

[45] Feb. 6, 1979

[54] IMMOBILIZED CATALYTICALLY ACTIVE SUBSTANCE AND METHOD OF PREPARING THE SAME

[75] Inventors: Ichiro Chibata, Suita; Tetsuya Tosa, Kyoto; Isao Takata, Takatsuki, all of Japan

[73] Assignee: Tanabe Seiyaku Co., Ltd., Osaka, Japan

[21] Appl. No.: 807,259

[22] Filed: Jun. 16, 1977

[30] Foreign Application Priority Data

Jul. 2, 1976 [JP] Japan .................................. 51-79346

[51] Int. Cl.$^2$ ........................... C07G 7/02; C12B 1/00
[52] U.S. Cl. .................................. 195/59; 195/53; 195/60; 195/63; 195/68; 195/31 F
[58] Field of Search ................... 195/63, 68, DIG. 11, 195/52-60

[56] References Cited

U.S. PATENT DOCUMENTS

| | | | |
|---|---|---|---|
| 3,223,593 | 12/1965 | Aldrich et al. | 195/63 |
| 3,278,392 | 10/1966 | Patchornik | 195/63 |
| 4,003,792 | 1/1977 | Mill et al. | 195/63 |

OTHER PUBLICATIONS

Annual Review of Biochemistry, vol. 35, Part II, pp. 873-904 (1966).
Biochemistry, vol. 31, No. 4, pp. 337-345 (Mar.-Apr. 1966) (A Translation of Biokhimiya).
Enzymologia, vol. 39, pp. 12-14 (1970).
Applied Microbiology, May 1974, pp. 878-885, vol. 27, No. 5.

*Primary Examiner*—Lionel M. Shapiro
*Attorney, Agent, or Firm*—Bierman & Bierman

[57] ABSTRACT

An enzyme or microorganism is entrapped within the gel matrix of a sulfated polysaccharide (said polysaccharide containing more than 10 w/w% of a sulfate moiety in its molecule) in the presence of ammonium ion, a metal ion, a water-soluble amine or a water-miscible organic solvent. The immobilized enzyme or microorganism thus obtained shows a high level of catalytic activity for a long period of time and can be used for continuous enzymatic reactions with substrates.

64 Claims, No Drawings

IMMOBILIZED CATALYTICALLY ACTIVE SUBSTANCE AND METHOD OF PREPARING THE SAME

This invention relates to an immobilized catalytically active substance and a method of preparing the same.

Enzymes and microorganisms have been used as catalysts to induce various chemical or enzymatic reactions. For example, they have been used as catalysts, not only in preparing organic acids, amino acids, 6-aminopenicillanic acid and so forth, but also in decomposing undesirable metabolic products such as urea. When they are used to catalyze reactions occuring in aqueous solutions, however, the separation or removal thereof from the reaction solution is conducted by boiling or acidifying said solution to denature the enzymes or microorganisms, and then filtering off the precipitates thereof. Thus, enzymes and microorganisms can be used only once and must be discarded thereafter.

Immobilized enzymes and microorganisms (i.e., enzymes and microorganisms bound to carriers) have become of great importance in recent years. Such immobilized preparations can be used as heterogeneous catalysts and, after the reactions are completed, may be readily removed from the reaction mixtures. Further, the immobilized enzymes or microorganisms may be used repeatedly or continuously to induce specific chemical changes in large amounts of substrates. In this connection, various methods of binding enzymes or microorganisms to carriers have been used, including (a) covalent binding of the enzymes or microorganisms to water-insoluble carriers; (b) ionic binding of the enzymes or microorganisms to carriers; (c) physical adsorption of the enzymes or microorganisms to carriers; (d) covalent cross-linking of the enzymes or microorganisms by bifunctional agents; (e) inclusion of the enzymes or microorganisms within the gel lattice of polymers; and (f) microencapsulation of the enzymes or microorganisms with semipermeable polymer membranes. Typical examples of these methods are seen in Annual Review of Biochemistry, Vol. 35, Part II, pages 873–903 (1966); Biochemistry (USSR) (English Translation), Vol. 31, pages 337–345 (1966); U.S. Pat. No. 3,278,392; Enzymologia, Vol. 39, pages 12–14 (1970); and Applied Microbiology, Vol. 27, pages 878–885 (1974). However, these immobilized enzymes or microorganisms, when packed in a column and used for reactions with substrates, tend to compact and deform thereby reducing the flow speed of the substrate solutions in the column.

Further, it is known that microorganisms are entrapped within the gel matrix of Japan agar by cooling an aqueous mixture of said agar and microorganisms (Japanese patent application laid open to the public under No. 95470/1975). But said Japan agar having microorganisms entrapped therein is unable to retain its shape in an aqueous media. When used for enzymatic reactions at a temperature higher than 40° C., it loses its network structure and is transformed into "sol" within a period as short as 60 minutes.

Apart from the above-mentioned prior art, enzymes and microorganisms may be entrapped within the gel matrix of carrageenan (i.e., a sulfated polysaccharide) by simply cooling an aqueous mixture of carrageenan and enzymes or microorganisms. As in case of Japan agar, however, the gel matrix of carrageenan obtained by this method is still too soft and unstable to use it in enzymatic reactions with substrates. For example, the gel structure of carrageenan obtained by this method, when used for enzymatic reactions with substrates in aqueous media, becomes loose and results in causes leakage of enzymes or microorganisms therefrom.

We have now found that a stable, immobilized, catalytically active substance can be obtained by entrapping enzymes or microorganisms within the gel matrix of a sulfated polysaccharide in the presence of ammonium ion, a metal ion, a water-soluble organic amine or a water-miscible organic solvent. In other words, when the immobilization or entrappment of enzymes and microorganisms with the sulfated polysaccharide is carried out in the presence of the above-mentioned ion, amine or solvent, the immobilized preparation thus obtained shows a high level of catalytic activity for a long period of time and at the same time the gel matrix thereof is sufficiently stable to prevent leakage of enzymes or microorganisms therefrom. Moreover, the sulfated polysaccharide, having enzymes or microorganisms entrapped therein in the presence of said ion, amine or solvent does not deform in an aqueous media. Even when used for enzymatic reactions by packing in a column, functions effectively so as to convert substrates to their conversion products. Further, we have found that the carrier-bound enzymes or microorganisms stated hereinbefore may also be employed for this immobilization method to improve the quality thereof. That is, the catalytic activity of enzymes or microorganisms bound to carriers can be maintained and the compacting or deformation thereof can be prevented or substantially reduced by entrapping the bound enzyme or microorganism within the gel matrix of said sulfated polysaccharide in the presence of ammonium ion, a metal ion, amine or a organic solvent.

The term "carrier-bound enzyme or microorganism" as used herein means the product produced by binding an enzyme or microorganism to a carrier by any of the six mechanisms (a) through (f) mentioned above and described in said publications.

According to the present invention, an immobilized catalytically active substance can be prepared by the steps of mixing a catalytically active substance with an aqueous solution of a sulfated polysaccharide, and contacting the aqueous mixture with ammonium ion, a metal ion, a water-soluble organic amine or a water-miscible organic solvent to give the gel matrix of the sulfated polysaccharide having the catalytically active substance entrapped therein.

The sulfated polysaccharide employed in the present invention should contain more than 10 w/w %, preferably between about 12 and 62 w/w %, of the sulfate (-SO$_3$H) moiety in its molecule. Representative examples of such polysaccharide sulfate ester include carrageenan, furcellaran and cellulose sulfate. Carrageenan refers to galactose sulfate esters which are obtained by extracting with water the sea weeds belonging to Rhodophyceae such as Ginartinacea and Solieriaceae (e.g., *Chondrus crispus, Gigartina acicularis, Eucheuma cottonii*). Among said galactose sulfate esters, kappa-carrageenan and iota-carrageenan are especially suitable for use in the present invention. Kappa-carrageenan consists mainly of $\beta$-D-galactopyranosyl-4-sulfate and 3,6-anhydro-$\alpha$-D-galactopyranose, and it contains between about 20 and 30 w/w % of sulfate (SO$_3$H) moiety in the molecule. On the other hand, iota-carrageenan is mainly a mixture of $\beta$-D-galactopyranosyl-4-sulfate and 3,6-anhydro-$\alpha$-D-galactopyranosyl-2-sulfate, and it contains between about 20 and 30 w/w % of the sulfate moiety in the molecule. Moreover, furcellaran is a sulfated polysaccharide which is obtained by extracting the the sea weeds of Furcellariaceae (e.g., *Furcellaria fastigiana*) with water, and consists mainly of D-galactose, 3,6-anhydro-D-galactose and the half-ester sulfate of these sugars. Furcellaran contains between about 12 and 16 w/w % of sulfate moiety in its molecule. Other suitable sulfated polysaccharides which may be employed in the present invention include cellulose sulfate containing between about 12 and 62 w/w % of the sulfate moiety in the molecule. Such cellulose sulfate is available in the market under the trade name "KELCO SCS" (KELCO Co., U.S.A.) (sulfate content: about 53%) or, if required, may be prepared by conventional esterification of cellulose with sulfuric acid.

In the present invention, a wide variety of enzymes may be employed as one of the catalytically active substances. Examples of such enzymes include oxidoreductase such as amino acid oxidase, catalase, xanthin oxidase, glucose oxidase, glucose-6-phosphate dehydrogenase, glutamate dehydrogenase, cytochrome C oxidase, tyrosinase, lactate dehydrogenase, peroxidase, 6-phosphogluconate dehydrogenase and malate dehydrogenase; transferases such as aspartate acetyltransferase, aspartate aminotransferase, glycine aminotransferase, glutamic oxalacetic aminotransferase, glutamic pyruvic aminotransferase, creatine phosphokinase, histamine methyltransferase, pyruvate kinase, hexokinase, ϵ-lysine acetyltransferase and leucine aminopeptidase; hydrolases such as asparaginase, acetylcholine esterase, aminoacylase, amylase, arginase, L-arginine deiminase, invertase, urease, uricase, urokinase, esterase, kallikrein, chymotrypsin, trypsin, thrombin, naringinase, nucleotidase, papain, hyaluronidase, plasmin, pectinase, hesperidinase, pepsin, penicillinase, penicillin amidase, phospholipase, phosphatase, lactase, lipase, ribonuclease and renin; lyases such as aspartate decarboxylase, aspartase, citrate lyase, glutamate decarboxylase, histidine ammonia-lyase, phenylalanine ammonia-lyase, fumarase, fumarate hydratase and malate synthetase; isomerases such as alanine racemase, glucose isomerase, glucose-phospate isomerase, glutamate racemase, lactate racemase and methionine racemase; and lygases such as asparagine synthetase, glutathion synthetase, glutamine synthetase and pyruvic acid synthetase. The above-mentioned enzymes are not necessarily pure, but crude enzyme solutions may be employed in the present invention. For example, the extracts of animal or plant tissues and the cell-free extracts of microorganisms may be preferably used as the enzyme solution. These extracts may be, of course, partially purified prior to using in the present invention. A mixture of two or more enzymes mentioned above may also be employed for the purpose of the present invention.

Catalytically active microorganisms such as bacteria, yeast, mold, lichens and protozoa are other examples of the catalytically active substances which are employed in the present invention. Any microorganisms which accumulate at least one of the above-mentioned enzymes within their living cells may be used as the catalytically active microorganisms of the invention. The microorganisms which can be used include, for example, *Achromobacter aquatilis, Achromobacter liquidum, Aspergillus oryzae, Aspergillus niger, Bacillus megatherium, Bacillus subtilis, Bacterium succinium, Brevibacterium ammonia-genes, Brevibacterium flavum, Corynebacterium glutamicum, Erwinia herbicola, Escherichia coli, Gluconobacter melanogenus, Lactobacillus bulgaris, Micrococcus ureae, Penicillium vinaceum, Proteus vulgaris, Pseudomonas aeruginosa, Pseudomonas dacunhae, Pseudomonas putidum, Sarcina lutea, Streptomyces griseus, Serratia marcescens, Streptomyces phaeochromogenus,* and Baker's yeast. These microorganisms may not necessarily be intact living cells, but may be lyophilized, heat-treated or treated with acetone prior to use thereof in the present invention.

Further, the carrier-bound enzyme or microorganism which is entrapped within the gel matrix of the sulfated polysaccharide according to the present invention comprises a water-insoluble, hydrophilic carrier having a catalytically active enzyme or microorganism bound thereto. The term "hydrophilic" as used herein means that the carrier is made wettable or swellable in water but is not substantially soluble therein. Any carriers having these properties may be utilized herein and the enzyme or microorganism may be bound thereto in any known manner, i.e., those mentioned hereinbefore. For example, polymers which may be used as carriers for the enzymes include diazotized p-aminobenzyl cellulose, diazotized p-aminobenzoyl cellulose, diazotized m-aminobenzyloxymethyl cellulose, the diazotized copolymer of p-aminophenylalanine and leucine, diazotized poly-p-aminostyrene, carboxymethyl cellulose, aminoethyl cellulose, carboxymethyl cross-linked dextran, carboxymethyl cellulose azide, ethylene-maleic anhydride copolymers, carboxymethyl cellulose isocyanate, cyanogen bromide-activated cellulose, cyanogen bromide-activated agarose, the aminosillan derivative of porous glass, bromoacetyl cellulose, iodoacetyl cellulose, dichloro-s-triazinyl cellulose, methacrylic acid-methacrylic acid-3-fluoro-4,6-dinitroanilide copolymers, diethylaminoethyl cellulose, triethylaminoethyl cellulose, diethylaminoethyl cross-linked dextran, acrylamide-methylenebisacrylamide copolymer, polyvinylalcohol, nylon, polyurea and the like. Examples of other carriers which may be used include charcoal, porous glass, acid clay, kaolinite, alumina and the like. On the other hand, polymers which may be used as carriers for the catalytically active microorganisms include acrylamide-methylenebisacrylamide copolymer, cellulose triacetate, carboxymethyl cellulose, diethylaminoethyl cellulose and the like. This listing is no way to be considered as all-inclusive and any other known carriers may also be used herein. Binding the enzyme or microorganisms to the hydrophilic carriers may be accomplished in a known manner, i.e., those described in the aforementioned publications. For example, when a carrier containing some groups which react with enzymes is employed, the enzymes react with the carrier at a temperature below which the enzymes are deactivated. The temperature at which specific enzymes are deactivated are well known to those skilled in the art and therefore need not be enumerated herein. Suffice to say that generally a temperature below 75° C., preferably between about 5° C. and 65° C., should be used. The reaction is preferably carried out in the presence of buffers to control the pH of the reaction mixture at a desired level, the particular pH being governed by the particular enzyme being bound, according to known techniques.

In carrying out the method of the present invention, an aqueous mixture of the sulfated polysaccharide and the catalytically active substance (i.e., the catalytically active enzyme or microorganism of the water-insoluble, hydrophilic, catalytically active carrier-bound enzyme or microorganism) may be prepared by any appropriate method. For example, the aqueous mixture may be readily obtained by dissolving the sulfated polysaccharide in water at a temperature of between about 30° C. and 90° C., and then mixing the sulfated polysaccharide solution with the catalytically active substance. Alternatively, said active substance may be employed in the form of a solution or suspension. For example, the catalytically active substance may be dissolved or suspended in water, a physiological saline solution or a buffer solution, and said solution or suspension may be added to the aqueous sulfated polysaccharide solution. Buffer solutions such as phosphate buffer solution, carbonate buffer solution and acetate buffer solution which are adjusted to a pH of between about 1 and 13, especially a pH of between about 4 and 10. These can be employed to dissolve or suspend said active substance therein. A suitable amount of the sulfated polysaccharide in the aqueous mixture is between about 0.05 and 20 w/w %, especially between about 0.4 and 10 w/w %. On the other hand, a suitable amount of the catalitically active substance for mixture with the sulfated polysaccharide is between about one mg and 50 g, especially between about 100 mg and 10 g, per gram of said sulfated polysaccharide. In admixing with the catalytically active substance or a solution or suspension thereof, it is preferred to use an aqueous polysaccharide solution the temperature of which is kept at a temperature of between about 30° and 70° C. Moreover, if required, proteins such as gelatin, collagen, albumin, globulin, zein, fibrinogen, myosin and casein; polysaccharides such as starch, cellulose and dextran; gums such as locust been gum, arabic gum, tragacanth gum, guar gum and Psyllium seed gum; alcohols such as glycerol, ethylenegylcol and polyethylene glycol; or synthetic polymers such as polyvinylalcohol and polyvinylpyrrolidone may be added to the above-mentioned aqueous mixture. That is, the ability of the sulfated polysaccharide gel to retain its shape in an aqueous media can be increased by adding between about 10 and 250 w/w % (based on the weight of the sulfated polysaccharide) of these materials to said aqueous mixture. Water-insoluble, inorganic porous materials may also be added to the aqueous mixture of the sulfated polysaccharide and the catalytically active substance in order to control the macromolecular structure or pore size of the sulfated polysaccharide gel matrix. Sellaite, siliceous sand, bentonite and activated charcoal are suitable as said water-insoluble, inorganic, porous materials. Additionally, if required, glutaraldehyde, tannins and the like may be further added to the aqueous mixture of the sulfated polysaccharide and the catalytically active substance prior to the subsequent contacting step. Addition of glutaraldehyde and tannins may be effective to increase the particle size of the enzymatically active substance thereby preventing the leakage of said active substance from the gel.

The aqueous mixture of the sulfated polysaccharide and the catalytically active substance is then contacted with ammonium ion, a metal ion having an atomic weight greater than 24, a water-soluble organic amine or a water-miscible organic solvent. Suitable examples of the metal ion which may be employed in the invention include alkali metal ions belonging to a group not lower than Series (4) in Mendeleev's Periodic Table (e.g., potassium, rubidium, cesium ions), alkali earth metal ions (e.g., magnesium, calcium, strontium, barium ions), aluminium ion, lead ion, manganese ion, ferric ion and ferrous ion. On the other hand, organic amines which are soluble in water may be employed. Such amines include, for example, an alkylenediamine of one to 20 carbon atoms (e.g., methylenediamine, N-methylmethylenediamine, N,N-dimethylmethylenediamine, ethylenediamine, trimethylenediamine, tetramethylenediamine, pentamethylenediamine, hexamethylenediamine, heptamethylenediamine, octamethylenediamine, nonamethylenediamine, decamethylenediamine, dodecamethylenediamine, eicosamethylenediamine); a phenylenediamine (e.g., p-phenylenediamine, m-phenylenediamine, o-phenylenediamine, dimethyl-p-phenylenediamine); a hydroxamate, hydrazide, alkyl ester or amide of a basic amino acid (e.g., lysine hydroxamate, histidine hydroxamate, tryptophan hydroxamate, lysine hydrazide, histidine hydrazide, lysine methyl ester, histidine methyl ester, lysine amide); a S-aminoalkyl-cysteine (e.g., S-aminomethyl-cysteine, S-(2-aminoethyl)-cysteine); an aminoalkylguanidine (e.g., agmatine); δ-hydroxy-lysine; melanine; an aminoalkyl-imidazole (e.g., histamine); an aminoalkyl-indol (e.g., serotonine); a guanidinoalkyl-aniline (e.g., 2-guanidinomethyl-aniline); an aminoalkyl-pyrrole (e.g., 2-aminomethyl-pyrrole); an aminoalkylpyrroline (e.g., 2-aminomethyl-pyrroline); an aminoalkylpyrrolidine (e.g., 2-aminomethyl-pyrrolidine); an aminoalkyl-thiazole (e.g., 2-aminomethyl-thiazole); an aminoalkyl-pyrazole (e.g., 3-aminomethyl-pyrazole); an aminoalkyl-thiazoline (e.g., 5-aminomethyl-thiazoline); an aminoalkyl-thiazolidine (e.g., 2-aminomethyl-thiazolidine); an aminoalkyl-pyridine (e.g., 2-aminomethyl-pyridine); an aminoalkyl-piperidine (e.g., 2-aminomethyl-piperidine); an aminoalkyl-pyrimidine (e.g., 5-aminomethyl-pyrimidine); an aminoalkyl-quinoline (e.g., 3-aminomethyl-quinoline); an aminoalkyl-morpholine (e.g., 4-aminomethyl-morpholine); a peptide (e.g., lysyl lysine, histidyl lysine, histidyl arginine, histidyl arginyl lysine, polylysine); and a polyalkyleneimine (e.g., polyethyleneimine). Further, suitable examples of the organic solvent which may be employed in the present invention include an alkanone having 3 to 5 carbon atoms (e.g., acetone), an alkanol having one to 3 carbon atoms (e.g., methanol, ethanol, propanol), dioxane, tetrahydrofuran, dimethylformamide, dimethylsulfoxide, ethyleneglycol and glycerin.

The treatment of the aqueous mixture of the sulfated polysaccharide and the catalytically active substance with the above-mentioned ammonium ion, metal ion or amine are preferably carried out at a temperature of between about − 5° and 70° C., especially at between about 0° and 55° C. It is preferred to carry out said treatment by adding the aqueous mixture to an aqueous solution of the ion or amine. The ion or amine should be employed at a concentration of between about 0.1 mM and 10 M, especially between about 10 mM and 2 M. On the other hand, the treatment of the aqueous mixture of the sulfated polysaccharide and the catalytically active substance with the water-miscible organic solvent may be preferably carried out at between about −5° and 70° C., especially at between about − 5° and 30° C. As compared with the preparations solidified with the ion or amine, the catalytically active substance immobilized with the polysaccharide in the presence of said water-miscible organic solvent may show a higher level of catalytic activity per volume of the preparations because the gel matrix of the sulfated polysaccharide is partially dehydrated and compacted with the solvent during the treatment thereof. Further, when *Escherichia* coli (one of aspartase-producing microorganisms) is immobilized with the sulfated polysaccharide in the presence of acetone or ethanol, it shows a catalytic activity about 2 to 3 times higher than that of its intact cells.

By any one of the above-mentioned operations, the sulfated polysaccharide is gelled and solidified, and thereby the catalytically active substance is entrapped within the resultant gel matrix of said polysaccharide. That is, the immobilized catalytically active substance obtained above comprises a catalytically active enzyme or microorganism or a water-insoluble, hydrophilic, catalytically active carrier-bound enzyme or microorganism entrapped within the gel matrix of the sulfated polysaccharide containing at least one of ammonium ion, the metal ion, the water-soluble organic amine and the water-miscible organic solvent. A preferred amount of the ion, amine or solvent which is to be contained in said gel matrix of the sulfated polysaccharide is between about $10^{-1}$ and $10^4$ millimoles, especially between about one and $10^3$ millimoles, per g of the sulfated polysaccharide employed. Depending on its use, the immobilized catalytically active substance can be shaped as particles, beads, plates, rods, tubes, films and fibers. For example, the immobilized active substance may be obtained in the form of particles or beads when the above-mentioned gellation step is carried out by adding, dropwise, the mixture of the sulfated polysaccharide and the catalytically active substance to the aqueous ion or amine solution or the water-miscible organic solvent. When the immobilized catalytically active substance is shaped as particles or beads, the size thereof suitable for use in the enzymatic reaction is between about 0.1 and 20 mm, especially between about one and 5 mm, in diameter. On the other hand, the fibers of the immobilized catalytically active substance may be obtained by introducing said aqueous mixture into the aqueous ion or amine solution or the water-miscible organic solvent through a small orifice of a container. Further, the immobilized active substance may be obtained as films or tubes by making a thin layer of the aqueous mixture of the sulfated polysaccharide and the catalytically active substance on the surface of glass plates, plastic plates, metal plates, glass tubes or plastic tubes, and then contacting said mixture with the aqueous ion or amine solution or the water-miscible organic solvent on the surface of said plates or tubes. The thickness of the membrane of the immobilized catalytically active substance thus obtained can be designated to determine the rate of diffusion of substrate to the vicinity of the catalytically active substance as well as the rate of diffusion of the products out of the reaction site. The thickness can be between about 0.01 and 5 mm, preferably between about 0.1 and one mm.

Concomitantly, if required, the immobilized catalytically active substance obtained above may be further treated with a gel-hardening agent in order to increase the hardness, elasticity and the ability to retain its shape in aqueous media. The term "gel-hardening agent" as used herein means a compound which can bind, through ionic, coordinate or covalent linkage to or be adsorbed by the immobilized catalytically active substance thereby increasing its hardness, elasticity and/or ability to retain its shape in aqueous media. Examples of such a gel-hardening agent include an aliphatic dialdehyde having 3 to 5 carbon atoms (e.g., glutaraldehyde, glyoxal), tannins, dihydroxyacetone, epichlorohydrin, ethyl chloroformate, hexamethylene diisocyanate, toluene diisocyanate, hexamethylene diisothiocyanate, a carbodiimide (e.g., 1-ethyl-3-(3-dimethylaminopropyl)-carbodiimide), a Woodward reagent (i.e., 2-ethyl-5-m-sulfophenyl-isoxazolium hydroxide), and a mixture of ammonia or an alkylenediamine having one to 20 carbon atoms (e.g., methylenediamine, ethylenediamine, trimethylenediamine, tetramethylenediamine, pentamethylenediamine, hexamethylenediamine, heptamethylenediamine, octamethylenediamine, nonamethylenediamine, decamethylenediamine, dodecamethylenediamine, eicosamethylenediamine) and an aliphatic dialdehyde having 3 to 5 carbon atoms (e.g., glutaraldehyde, glyoxal). The treatment of the immobilized catalytically active substance with the gel-hardening agent may be preferably carried out by dissolving the gel-hardening agent in a solvent, and then immersing said immobilized substance therein. It is preferred to carry out the treatment at a temperature of between about 0° and 50° C., especially between about 5° and 37° C. It is also preferred to use a solution containing between about 0.01 and one gram (per ml of the solvent) of the gel-hardening agent. When the immobilized catalytically active substance is hardened by treating it with an aliphatic dialdehyde (e.g., glutaraldehyde, glyoxal) in the presence of ammonia or an alkylenediamine (e.g., hexamethylenediamine), the immobilized preparation obtained in the form of a shiff-base may be further treated with a reducing agent such as sodium Since the immobilized catalytically active substance treated with the gel-hardening agent has an increased ability to retain its shape in aqueous media, it may be suitable for use in a long-term continuous enzymatic reactions with substrates. In addition, the catalytic activity of the immobilized active substance treated with the gel-hardening agent may often be more stable than that of the non-treated substance. For example, when aminoacylase, glucose isomerase, *Pseudomonas dacunhae* (L-aspartate β-decarboxylase-producing microorganism), *Streptococcus faecalis (glucose isomerase-producing microorganism)* and *E. coli* (aspartase-producing microorganism) immobilized by the aforementioned method of the invention are further treated with the gel-hardening agent, they maintain their catalytic activity for at least about 2 times or more longer period of time.

The immobilized catalytically active substance of the present invention shows a high level of catalytic activity for a long period of time. The enzymes or microorganisms or the carrier-bound enzymes or microorganisms are retained firmly in the gel matrix of the sulfated polysaccharide whereas molecules of substrates and reaction products, of smaller size, will be able to move freely in the polymeric network of said polysaccharide. An enzyme or microorganism preparation (hereinafter referred to as "the control sample") which is obtained by simply cooling an aqueous mixture of the sulfated polysaccharide and enzymes or microorganisms is still unsuitable for use in the enzymatic reactions with substrates. For example, when an aqueous substrate solution is passed through a column charged with the control sample, it deforms within a short period of time and does not function effectively to convert substrates to their conversion products. As compared with said control sample, however, the immobilized catalytically active substance of the present invention has a remarkably greater ability to retain its shape in an aqueous media and, even when packed in a column, the enzymatic reaction thereof with substrates can be continued for a longer period of time without repacking or agitating the column. Moreover, the polysaccharide gel of the above-mentioned control sample is unstable and easily transformed into "sol" (i.e., a colloidal solution) at about 30° to 40° C. This inevitably causes leakage of the enzymes or microorganisms from the gel matrix. Unlike said control sample, however, the immobilized catalitically active substance of the invention has excellent heat-stability. For example, the polysaccharide gel of the catalytically active substance of the invention is not transformed into "sol" even at a temperature higher than 40° C. and it can be employed for enzymatic reactions at such high temperatures as 60° to 70° C. without leakage of the enzymes or microorganisms therefrom. Further, the polysaccharide gel of the immobilized catalytically active substance of the invention has excellent hardness and elasticity and can be shaped into any desired form such as particles, beads, films, tubes and fibers according to its intended use. On the otherhand, whereas the gel of the above-mentioned control sample is too soft to shape it as above. As briefly mentioned hereinbefore, the carrier-bound enzyme or microorganism becomes compacted and deformed when in use and under such conditions can not function effectively to convert substrates to their conversion products. However, the compacting, deformation and/or channelling of the carrier-bound enzyme or microorganism is materially reduced by entrapping it within the gel matrix of the sulfated polysaccharide according to the present invention. This may make it unnecessary to repack or agitate the column of the bound-enzyme or microorganism during the enzymatic reactions thereof with substrates.

The immobilized catalytically active substance of the invention can be used for any of a wide variety of enzymatic reactions which have been conducted by the use of enzyme, living microorganisms or carrier-bound enzymes or microorganisms. For example, aminoacylase or an aminoacylase-producing microorganism (e.g., *Aspergillus orizae*) entrapped according to the present invention may be used in preparing L-amino acids by asymmetric hydrolysis of N-acyl-DL-amino acids. The entrapped aspartase or aspartase-producing microorganism (e.g., *Escherichia coli*) can be used, instead of the corresponding intact enzyme or microorganism, for the enzymatic reaction with fumaric acid and ammonia to produce L-aspartic acid. When asparaginase or an asparaginase-producing microorganism (e.g., *Proteus vulgaris*) is immobilized according to the invention, said immobilized enzyme or microorganism may be used for enzymatic reaction with L-asparagine to decompose it into L-aspartic acid and ammonia. L-alanine can be prepared from L-aspartic acid by using the entrapped aspartate β-decarboxylase or aspartate β-decarboxylase-producing microorganism (e.g., *Pseudomonas dacunhae*). On the other hand, each one of L-arginine deiminase (or a L-arginine deiminase-producing microorganism such as *Pseudomonas putidum*), L-histidine ammonia-lyase (or a L-histidine ammonia-lyase-producing microorganism such as *Achromobacter liquidum*) and fumarase (or a fumarase-producing microorganism such as *Brevibacterium flavum*) entrapped according to the present invention can be used for enzymatic reactions with L-arginine, L-histidine or fumaric acid to produce L-citrulline, urocanic acid or L-malic acid, respectively. Moreover, when a L-isoleucine or arginine-producing microorganism (e.g., *Serratia marcescens, Bacillus subtilis*) is immobilized according to the present invention, L-isoleucine or arginine are prepared by cultivating said immobilized microoganism in a conventional nutrient medium containing glucose. Fructose may be prepared from glucose by enzymatic reaction thereof with the entrapped glucose isomerase or glucose isomerase-producing microorganism (e.g., *Streptomyces phaeochromogenes, Streptomyces griseus*). 6-Aminopenicillanic acid may be prepared from penicillins by using the entrapped penicillin amidase or penicillin amidase-producing microorganism (e.g., *Escherichia coli*). Concomitantly, urea may be decomposed into ammonia and carbon dioxide by using the entrapped urease or urease-producing microorganism (e.g., *Sarcina lutea*) of the invention. The reaction conditions which have been used for the enzymatic reactions of intact enzymes or microorganisms with their usual substrates can be employed in carrying out the enzymatic reaction of the immobilized catalytically active substance of the invention. In carrying out said enzymatic reactions of the immobilized catalytically active substance, it is generally preferred to add to the reaction solutions a small amount (e.g., between about 0.1 mM and 10 M, especially between about 10 mM and 5 M) of ammonium ion, metal ion, water-soluble organic amine or water-miscible organic solvent used in the gellation step mentioned hereinbefore. When the immobilized catalytically active substance of the invention treated with the gel-hardening agent is employed, however, the enzymatic reaction thereof with substrates may be carried out without said ion, amine or solvent. For example, when the immobilized glucose isomerase preparation of the invention, pre-treated with a mixture of glutaraldehyde and hexamethylenediamine, is employed for the enzymatic reaction with glucose, said enzymatic reaction can be continued for a period of 120 days or longer in the absence of the ion, amine or solvent. Further, the reactions of the immobilized catalytically active substance with substrates may be carried out by in a conventional manner. For example, the substrate can be dissolved in water. The immobilized catalytically active substance is suspended in the aqueous substrate solution, and the suspension is stirred. Since the immobilized catalytically active substance is insoluble in water, after the reaction it can be readily recovered by filtration or centrifugation and the reaction products are recovered from the filtrate or supernatant solution. Alternatively, the above-mentioned enzymatic reactions may be carried out by a column method. The column method enables the reaction to be carried out in a successive manner. For example, the immobilized catalytically active substance is packed in a column, and an aqueous substrate solution is passed through the column at a suitable flow rate. An aqueous solution containing the reaction product is obtained as an effluent. In carrying out the enzymatic reaction, the rate of conversion of substrates to their conversion products mainly depends on the catalytic activity of the immobilized active substance, the temperature and the reaction period. In case of the column method, however, the optimum reaction conditions for complete conversion of substrates to their conversion products may be readily obtained by adjusting the flow rate of the substrate solutions.

Practical and presently-preferred embodiments of the present invention are shown in the following Examples.

EXAMPLE 1

(1) 4 mg of aminoacylase (20 units/mg) obtained from Aspergillus oryzae are dissolved in 5 ml of water. 20 ml of an aqueous 4.4% carrageenan (manufactured by The Kopenhagen Pectin Factory Ltd., under the trade name "GENU GEL Type WG") solution previously warmed to 45° C. are added to the aminoacylase solution, and the mixture is added dropwise to an aqueous 2% potassium chloride solution. The resultant gel particles (about 3 mm in diameter) are collected by filtation, and then washed with an aqueous 2% potassium chloride solution. 18.1 g (wet form) of an immobilized aminoacylase preparation are obtained. It shows an aminoacylase activity of 2.1 units/g.

[One unit of aminoacylase is defined as the enzymatic activity which produces one micromole of L-methionine by reaction with N-acetyl-DL-methionine at 37° C. at pH 7.0 for one hour. The reaction with N-acetyl-DL-methionine is conducted by adding 15 g of the immobilized preparation to 40 ml of an aqueous 0.6 M N-acetyl-DL-methionine solution (adjusted to pH 7.0 with potassium hydroxide) containing $5 \times 10^{-4}$ M cobaltous chloride, and then shaking the mixture at 37° C. for one hour. The amount of L-methionine produced is assayed colorimetrically by the ninhydrin method.]

(2) 15 g of the immobilized aminoacylase preparation obtained in paragraph (1) are packed in a column (1.6 cm in diameter and 14 cm in height). An aqueous 0.6 M N-acetyl-DL-methionine solution (adjusted to pH 7.0 with potassium hydroxide) containing $5 \times 10^{-4}$ M cobaltous chloride is passed through the column at 37° C. at a flow rate of 10 ml/hr. The enzymatic activity of the immobilized aminoacylase preparation is assayed at intervals. The results are shown in Table 1. The half-life of the enzymatic activity of the immobilized aminoacylase preparation is about 60 days. As seen from this data, the immobilized aminoacylase preparation shows a high enzymatic activity for a long period of time when used for the continuous enzymatic reaction.

On the other hand, just for comparison, immobilized preparations are prepared by covalently binding aminoacylase to iodoacetyl-cellulose according to the method described in Fermentation Technology Today, pages 383-389 (1972), or by entrapping aminoacylase within the lattice of polyacrylamide according to the method described in the above-mentioned literature. The enzymatic activity of these immobilized preparations decreases to 50% of their initial activity only after the above-mentioned continuous enzymatic reaction for 5 or 30 days.

Table 1

| Operation period (days) | Aminoacylase activity (units) | Potency ratio of enzymatic activity* (%) |
|---|---|---|
| 1 | 32 | 100 |
| 2 | 30 | 94 |
| 5 | 29 | 91 |
| 7 | 29 | 91 |
| 9 | 29 | 91 |

Note:
*Potency ratio of enzymatic activity is calculated by the following formula:

$$\left[ \frac{\text{Activity of the immobilized enzyme or microbial cells preparation estimated after a period of time specified in Table}}{\text{Initial activity of the immobilized enzyme or microbial cells preparation}} \right] \times 100$$

EXAMPLE 2

5 mg of aminoacylase (20 units/mg) obtained from Aspergillus oryzae are dissolved in 5 ml of water. 20 ml of an aqueous 4.4% carrageenan (the trade name "GENU GEL Type WG") solution previously warmed to 45° C. are added to the aminoacylase solution, and the mixture is added dropwise to an aqueous 0.2 M N-acetyl-DL-methionine solution (adjusted to pH 7.0 with potassium hydroxide) containing $5 \times 10^{-4}$ M cobaltous chloride. The resultant gel particles (about 3 mm in diameter) are collected by filtration. 19.1 g (wet form) of an immobilized aminoacylase preparation are obtained. It shows an aminoacylase activity of 4.7 units/g.

EXAMPLE 3

5 mg of aminoacyhlase (20 units/mg) obtained from Aspergillus oryzae are dissolved in 5 ml of water. 20 ml of an aqueous 4.4% carrageenan (the trade name "GENU GEL Type WG") solution previously warmed to 45° C. are added to the aminoacylase solution, and the mixture is added dropwise to an aqueous 0.2 M N-acetyl-DL-tryptophan solution (adjusted to pH 7.0 with potassium hydroxide) containing $5 \times 10^{-4}$ M cobaltous chloride. The resultant gel particles (about 3 mm in diameter) are collected by filtration. 18.6 g (wet form) of an immobilized aminoacylase preparation are obtained. It shows an aminoacylase activity of 3.6 units/g.

EXAMPLE 4

*Brevibacterium ammoniagenes* IAM (Institute of Applied Microbiology, Tokyo University, Japan) 1645 is inoculated into 500 ml of an aqueous medium (pH 7.0) containing 2.0% of glucose, 0.5% of fumaric acid, 0.2% of urea, 0.2% of monopotassium phosphate, 0.05% of magnesium sulfate 7 hydrate and 1.0% of corn steep liquor. The medium is cultivated at 30° C. for 24 hours under shaking. Then, the microbial cells are collected by centrifugation. 10 g of the microbial cells are suspended in 100 ml of a 0.01 M phosphate buffer solution. The microbial cells in the suspension are disrupted with a sonicator at 9 Kc for 10 minutes, and then centrifuged. Ammonium sulfate is added gradually to the supernatant solution, and precipitates which are salted out from partially saturated ammonium sulfate solution (40-70% saturation) are collected by centrifugation. The precipitates are dissolved in 15 ml of a 0.01 M phosphate buffer solution (pH 7.0), and the solution is dialyzed overnight against a 0.01 M phosphate buffer solution. The dialyzed solution is used as a fumarase solution.

2 ml of a 0.01 M phosphate buffer solution are added to one ml of the fumarase solution. 12 ml of an aqueous 4.2% carrageenan (the trade name "GENU GEL Type WG") solution previously warmed to 40° C. are added to the fumarase solution, and the mixture is added dropwise to an aqueous 2% potassium chloride solution. The resultant gel particles (about 3 mm in diameter) are collected by filtration. 15 g (wet form) of an immobilized fumarase preparation are obtained. It shows a fumarase activity of 111.6μ moles/hr/g. Yield of activity[={(Enzymatic activity of the immobilized preparation obtained from one gram of the intact enzyme or microbial cells) ÷ (Enzymatic activity of one gram of the intact enzyme or microbial cells)} × 100] : 62%.

[Fumarase activity is indicated in terms of micromoles of L-malic acid which are produced by reaction with potassium fumarate. The reaction with potassium fumarate is conducted by adding 15 g of the immobilized preparation to 30 ml of a 0.2 M potassium furmarate-0.01 M potassium phosphate buffer solution and shaking the mixture at 37° C. for one hour. After the reaction, hydrochloric acid is added to the mixture, followed by filtering to remove the precipitates of fumaric acid. Then, the amount of L-malic acid (i.e., L-malic acid contained in the filtrate) is assayed colorimetrically by using 2,7-naphthalenediol as a coloring agent.]

EXAMPLE 5

*Escherichia coli* ATCC 11303 is inoculated into 500 ml of an aqueous medium (pH 7.0) containing 3% of ammonium fumarate, 0.2% of dipotassium phosphate, 0.05% of magnesium sulfate 7 hydrate, 4% of corn steep liquor and 0.05% of calcium carbonate. The medium is cultivated at 37° C. for 24 hours under shaking. Then, the microbial cells are collected by centrifugation. 8 g of the microbial cells are suspended in 8 ml of water. The microbial cells in the suspension are disrupted with a sonicator at 9 Kc for 15 minutes, and then centrifuged. Ammonium sulfate is added gradually to the supernatant solution, and precipitates which are salted out from partially saturated ammonium sulfate solution (30–50% saturation) are collected by centrifugation. The precipitates are dissolved in 5 ml of water, and the solution is dialyzed overnight against water. The dialyzed solution is used as an aspartase solution.

2 ml of the aspartase solution obtained above are mixed with 12 ml of an aqueous 3.2% carrageenan (the trade name "GENU GEL Type WG") solution at 37° C. The mixture is added dropwise to an aqueous 2% potassium chloride solution. The resultant gel particles (about 3 mm in diameter) are collected by filtration. 10.6 g (wet form) of an immobilized aspartase preparation are obtained. It shows an aspartase activity of 2,868$\mu$ moles/hr/g. Yield of Activity: 46%.

[Aspartase activity is indicated in terms of micromoles of L-aspartic acid which are produced by reaction with ammonium fumarate at 37° C. at pH 8.5. The reaction with ammonium fumarate is conducted by adding 2 g of the immobilized aspartase preparation to 30 ml of an aqueous 1 M ammonium fumarate solution (pH 8.5) containing 1 mM magnesium chloride, and then shaking the mixture at 37° C. for one hour. The amount of L-aspartic acid produced is bioassayed by using leuconostoc mesenterioides P-60(J. Biol. Chem., 172, 15(1948).]

EXAMPLE 6

10 mg of glucose isomerase (223 units/mg) obtained from Streptomyces phaeochromogenus are dissolved in 5 ml of water. 20 ml of an aqueous 4.4% carrageenan (the trade name "GENU GEL Type WG") solution previously warmed to 45° C. are added to the glucose isomerase solution, and the mixture is added dropwise added to an aqueous 2% potassium chloride solution. The resultant gel particles (about 3 mm in diameter) are collected by filtration, and then washed with an aqueous potassium chloride solution. 23.0 g (wet form) of an immobilized glucose isomerase preparation are obtained. It shows a glucose isomerase activity of 13.6 units/g.

[One unit of glucose isomerase is defined as the enzymatic activity which produces one micromole of fructose by reaction with glucose at 37° C. at pH 7.0 for one minute. The reaction with glucose is conducted by adding 2 g of the immobilized glucose isomerase preparation to 20 ml of an aqueous 0.1 M glucose solution (pH 7.0) containing 0.01 M of magnesium sulfate, 1 mM cobaltous chloride and 0.1 M sodium sulfite, and then shaking the mixture at 37° C. for one hour. The amount of fructose produced is measured by the cysteinecarbazole-sulfuric acid method.]

EXAMPLE 7

20 mg of aminoacylase (20 units/mg) obtained from Aspergillus oryzae are dissolved in 4 ml of water. 16 ml of an aqueous 4.4% carrageenan (the trade name "GENU GEL Type WG") solution previously warmed to 45° C. are added to the aminoacylase solution, and the mixture is added dropwise to an aqueous 1 M ammonium chloride solution. The resultant gel particles (about 3 mm in diameter) are collected by filtration, and then washed with an aqueous 2% potassium chloride solution. 18.8 g (wet form) of an immobilized aminoacylase preparation are obtained. It shows an aminoacylase activity of 66 units/g.

EXAMPLE 8

*Pseudomonas dacunhae* IAM 1152 is inoculated into 500 ml of an aqueous medium (pH 7.0) containing 0.5% of ammonium fumarate, 1.0% of sodium fumarate, 0.55% of corn steep liquor, 1.8% of peptone, 0.05% of monopotassium phosphate and 0.01% of magnesium sulfate 7 hydrate. The medium is cultivated at 30° C. for 24 hours under shaking. Then, the microbial cells are collected by centrifugation. 10 g of the microbial cells are suspended in 100 ml of a 0.01 M phosphate buffer solution. The microbial cells in the suspension are disrupted with a sonicator at 9 Kc for 10 minutes, and then centrifuged. The supernatant solution thus obtained is used as an aspartate $\beta$-decarboxylase solution.

One ml of the aspartate $\beta$-decarboxylase solution obtained above is treated in the same manner as described in Example 4. 12 g (wet form) of an immobilized aspartate $\beta$-decarboxylase preparation are obtained as gel particles of about 3 mm in diameter. It shows an aspartate $\beta$-decarboxylase activity of 36$\mu$ moles/hr/g. Yield of Activity: 57%.

[Aspartate $\beta$-decarboxylase activity is indicated in terms of micromoles of L-alanine which are produced by reaction with 0.2 M L-aspartic acid. The reaction with L-aspartic acid is conducted by adding 12 g of the immobilized preparation to 30 ml of an aqueous 0.2 M ammonium L-asparaginate solution (pH 5.5) containing $10^{-4}$ M pyridoxal phosphate, and shaking the mixture at 37° C. for one hour. The amount of L-alanine produced is bioassayed by using Leuconostoc mesenterioides P-60.]

EXAMPLE 9

2 ml of an aspartase solution obtained in the same manner as described in Example 5 are mixed with 12 ml of an aqueous 3.2% carrageenan (the trade name "GENU GEL Type WG") solution at 37° C. The mixture is added dropwise to an aqueous 1 M ammonium fumarate solution (pH 8.5). The resultant gel particles (about 3 mm in diameter) are collected by filtration. 9.4 g (wet form) of an immobilized aspartase preparation are obtained. It shows an aspartase activity of 1,966$\mu$ moles/hr/g. Yield of Activity: 52.4%.

EXAMPLE 10

100 mg of aminoacylase (20 units/mg) obtained from Aspergillus oryzae are dissolved in 4 ml of water. 16 ml of an aqueous 4.4% carrageenan (the trade name "GENU GEL Type WG") solution previously warmed to 40° C. are added to the aminoacylase solution, and the mixture is added dropwise to an aqueous 0.5 M hexamethylenediamine solution (adjusted to pH 7.0 with hydrochloric acid). The resultant gel particles (about 3 mm in diameter) are collected by filtration, and then washed with an aqueous one % potassium chloride solution. 18.9 g (wet form) of an immobilized aminoacylase preparation are obtained. It shows an aminoacylase activity of 11.9 units/g.

EXAMPLE 11

100 mg of aminoacylase (20 units/mg) obtained from Aspergillus oryzae are dissolved in 4 ml of water. 16 ml of an aqueous 4.4% carrageenan (the trade name "GENU GEL Type WG") solution previously warmed to 40° C. are added to the aminoacylase solution, and the mixture is added dropwise to an aqueous 0.5 M nonamethylenediamine solution (adjusted to pH 7.0 with hydrochloric acid). The resultant gel particles (about 3 mm in diameter) are collected by filtration, and then washed with an aqueous one % potassium chloride soluton. 19.1 g (wet form) of an immobilized aminoacylase preparation are obtained. It shows an aminoacylase activity of 13.5 units/g.

EXAMPLE 12

200 mg of aminoacylase (20 units/mg) obtained from Aspergillus oryzae are dissolved in 4 ml of water. 16 ml of an aqueous 4.4% carrageenan (the trade name "GENU GEL Type WG") solution containing 5% of gelatin (said carrageenan solution being previously warmed to 45° C.) are added to the aminoacylase solution, and the mixture is dropwise added to an aqueous 2% potassium chloride solution. The resultant gel particles (about 3 mm in diameter) are collected by filtration, and then washed with an aqueous 2% potassium chloride solution. 19.4 g (wet form) of an immobilized aminoacylase preparation are obtained. It shows an aminoacylase activity of 37.5 units/g.

EXAMPLE 13

(1) 100 mg of aminoacylase (20 units/mg) obtained from Aspergillus oryzae are dissolved in 50 ml of water. One g (dry form) of diethylaminoethyl cross-linked dextran (manufactured by Pharmacia Fine Chemicals under the trade name "DEAE-Sephadex A-25") is added to the solution, and the mixture is stirred at room temperature for one hour. DEAE-Sephadex-bound aminoacylase thus obtained is collected by filtration. Said DEAE-Sephadex-bound aminoacylase is suspended in 5 ml of water. 20 ml of an aqueous 4.4% carrageenan (the trade name "GENU GEL Type WG") solution previously warmed to 40° C. are added to the suspension, and the mixture is added dropwise to an aqueous 0.1 M potassium chloride solution. The resultant gel particles (about 3 mm in diameter) are collected by filtration. 29.8 g (wet form) of an immobilized aminoacylase preparation are obtained. It shows an aminoacylase activity of 32.9 units/g.

(2) 14.9 g of the immobilized aminoacylase preparation obtained in paragraph (1) are packed in a column (1.6 cm in diameter and 14 cm in height). An aqueous 0.6 M N-acetyl-DL-methionine solution (adjusted to pH 7.0 with potassium hydroxide) containing $5 \times 10^{-4}$ M cobaltous chloride is passed through the column at 37° C. at a flow rate of 10 ml/hr. The enzymatic activity of the immobilized aminoacylase preparation is assayed at intervals. The results are shown in Table 2. The half-life of the enzymatic activity of the immobilized aminoacylase preparation is about 120 days. As seen from these data, the immobilized aminoacylase preparation shows a high enzymatic activity for a long period of time when used for the continuous enzymatic reaction.

Table 2

| Operation period (days) | Aminoacylase activity (units) | Potency ratio of enzymatic activity* (%) |
|---|---|---|
| 0 | 25 | 100 |
| 5 | 26 | 100 |
| 10 | 24 | 96 |
| 15 | 25 | 100 |
| 20 | 25 | 100 |

Note:
*Potency ratio of enzymatic activity is calculated by the formula shown in the foot-note of Table 1.

EXAMPLE 14

20 mg of aminoacylase (20 units/mg) obtained from Aspergillus oryzae are dissolved in one ml of water, and 4 ml of an aqueous 4% tannic acid solution (adjusted to pH 7.0 with sodium hydroxide) are added thereto. 20 ml of an aqueous 4.4% carrageenan (the trade name "GENU GEL Type WG") solution previously warmed to 45° C. are added to the aminoacylase-tannic acid solution. Then, the mixture is added dropwise to an aqueous 0.1 M potassium chloride solution. The resultant gel particles (about 3 mm in diameter) are collected by filtration, and washed with an aqueous 0.1 M potassium chloride solution. 24.0 g (wet form) of an immobilized aminoacylase preparation are obtained. It shows an aminoacylase activity of 0.6 unit/g.

EXAMPLE 15

200 mg of aminoacylase (20 units/mg) obtained from Aspergillus oryzae are dissolved in 4 ml of water. 16 ml of an aqueous 4.4% carrageenan (the trade name "GENU GEL Type WG") solution containing 5% of gelatin (said carrageenan solution being previously warmed to 45° C.) are added to the aminoacylase solution, and the mixture is added dropwise to an aqueous one M ammonium chloride solution. The resultant gel particles (about 3 mm in diameter) are collected by filtration. The gel particles thus obtained are added to a mixture of 20 ml of an aqueous one M ammonium chloride solution and 1.6 ml of an aqueous 25% glutaraldehyde solution, and the mixture is stirred at 4° C. for 30 minutes. Then, the gel particles are collected by filtration, and washed with an aqueous 2% potassium chloride solution. 18.6 g (wet form) of an immobilized aminoacylase preparation are obtained. It shows an aminoacylase activity of 21.5 units/g.

EXAMPLE 16

10 mg of glucose isomerase (223 units/mg) obtained from Streptomyces phaeochromogenus are dissolved in one ml of water, and 4 ml of an aqueous tannin solution (adjusted to pH 7.0 with sodium hydroxide) are added thereto. The glucose isomerase solution is allowed to stand at 45° C. for 5 minutes, and then 20 ml of an aqueous 4.4% carrageenan (the trade name "GENU GEL Type WG") solution previously warmed to 45° C. are added thereto. The mixture is added dropwise to an aqueous 2% potassium chloride solution. The resultant gel particles (about 3 mm in diameter) are collected by filtration, and washed with an aqueous 2% potassium chloride solution. 25.4 g (wet form) of an immobilized glucose isomerase preparation are obtained. It shows a glucose isomerase activity of 1.5 units/g.

EXAMPLE 17

10 mg of glucose isomerase (223 units/mg) obtained from Streptomyces phaeochromogenus are dissolved in one ml of water. 4 ml of an aqueous persimmon tannin solution (tannin content: 2.5 mg/ml) are added to the glucose isomerase solution. Then, the glucose isomerase-persimmon tannin solution is allowed to stand at 45° C. for 5 minutes, and an aqueous 4.4% carrageenan (the trade name "GENU GEL Type WG") solution previously warmed to 45° C. are added thereto. The mixture is added dropwise to an aqueous 2% potassium chloride solution. The resultant gel particles (about 3 mm in diameter) are collected by filtration, and washed with an aqueous 2% potassium chloride solution. 23.2 g (wet form) of an immobilized glucose isomerase preparation are obtained. It shows a glucose isomerase activity of 5.2 units/g.

EXAMPLE 18

10 mg of vegetable proteolytic enzyme "papain" (3.1μ moles/minute/mg of protein) are dissolved in 6 ml of a 0.02 M citrate-phosphate buffer solution (pH 6.2) containing 0.005 M cysteine and 0.01 M ethylenediamine tetra-acetic acid. 25 ml of an aqueous 4% carrageenan (the trade name "GENU GEL Type WG") solution previously warmed to 40° C. are added to the papain solution, and the mixture is added dropwise to an aqueous 2% potassium chloride solution. The resultant gel particles (about 3 mm in diameter) are collected by filtration. 30 g (wet form) of an immobilized papain preparation are obtained. Yield of Activity: 57%.
[One unit of papain activity is defined as the enzymatic activity which decomposes one μ mole of α-benzoyl-arginine ethyl ester by reacting with said arginine ester at pH 6.2 for one minute. The reaction with α-benzoyl-arginine ethyl ester is conducted by adding 5 g of the immobilized preparation to 10 ml of a 0.02 M citrate-phosphate buffer solution (pH 6.2) containing 0.1 M benzoyl-arginine ethyl ester, and shaking the mixture at 37° C. for 10 minutes. The remaining amount of said benzyl arginine ester is measured in accordance with the J. R. Kimmel et al's method described in J. Biol. Chem., 207, 515 (1954).]

EXAMPLE 19

Escherichia coli ATCC 9637 is inoculated into 1,000 ml of an aqueous medium (pH 7.0) containing 0.2% of phenoxyacetic acid, 2% of peptone, 0.5% of yeast extract, 0.5% of sodium L-gultamate, 0.3% of monopotassium phosphate, 0.7% of dipotassium phosphate, 0.02% of magnesium sulfate 7 hydrate and 0.02% of ferric chloride 6 hydrate. The microbial cells are collected by centrifugation. The microbial cells thus obtained are suspended in 13 ml of an aqueous physiological saline solution. 52 ml of an aqueous 3.2% carrageenan (the trade name "GENU GEL Type WG") solution previously warmed to 40° C. are added to the suspension, and the mixture is added dropwise to an aqueous 2% potassium chloride solution. The resultant gel particles (about 3 mm in diameter) are collected by filtration. 60.7 g (wet form) of an immobilized Escherichia coli preparation are obtained. It shows a penicillin amidase activity of 1,114μ moles/hr/g. Yield of Activity: 90%. [Penicillin amidase activity is assayed in accordance with the J. Bomstein's method described in Analytical Chemistry, Vol. 37, pp. 576–578 (1965).]

EXAMPLE 20

(1) Brevibacterium ammoniagenes IAM 1645 is inoculated into 100 ml of an aqueous medium (pH 7.0) containing the same ingredients as described in Example 4. The medium is cultivated at 30° C. for 24 hours under shaking. Then, the microbial cells are collected by centrifugation. The microbial cells thus obtained are suspended in 4 ml of an aqueous physiological saline solution. 16 ml of an aqueous 2.5% carrageenan (the trade name "GENU GEL Type WG") solution previously warmed to 37° C. are added to the suspension, and the mixture is added dropwise to an aqueous 2% potassium chloride solution. The resultant gel particles (about 3 mm in diameter) are collected by filtration. 20 g (wet form) of an immobilized Brevibacterium ammoniagenes preparation are obtained.

10 g of the immobilized Brevibacterium ammoniagenes preparation obtained above are added to 30 ml of an aqueous one M potassium fumarate solution (pH 7.0) containing 0.3% of ox bile extract. The mixture is allowed to stand at 37° C. for 20 hours. After said treatment, the immobilized Brevibacterium ammoniagenes preparation is washed with an aqueous one % potassium chloride solution. The immobilized preparation thus obtained shows a fumarase activity of 5,790μ moles/hr/g of microbial cells. Yield of Activity: 60%

(2) 20 g of the immobilized Brevibacterium ammoniagenes preparation obtained in paragraph (1) are packed in a column (1.6 cm in diameter and 12 cm in height). An aqueous 1 M potassium fumarate solution (pH 7.0) is passed through the column at 37° C. at a flow rate specified in Table 3. The amount of L-malic acid in the effluent is assayed in the same manner as described in Example 4, and the percentage conversion of potassium fumarate into L-malic acid is calculated therefrom. The results are shown in Table 3.

Table 3

| Flow rate (ml/hr) | Conversion (%) to L-malic acid |
|---|---|
| 3.5 | 82 |
| 6 | 80 |
| 9 | 70 |
| 12 | 62 |
| 20 | 40 |
| 45 | 23 |

EXAMPLE 21

(1) Pseudomonas putidum ATCC 4359 is inoculated in 100 ml of an aqueous medium (pH 6.2) containing one % of glucose, one % of yeast extract, 0.5% of polypeptone, 0.5% of L-arginine hydrochloride, 0.1% of ammonium chloride, 0.1% of dipotassium phosphate, 0.05% of magnesium sulfate 7 hydrate, 0.01% of manganous sulfate 4 hydrate, 0.0005% of ferrous sulfate 7 hydrate and 0.02% of sodium chloride. The medium is cultivated at 30° C. for 24 hours under shaking. The microbial cells are collected by centrifugation. The microbial cells thus obtained are treated in the same manner as described in Example 20. 20 g (wet form) of an immobilized Pseudomonas putidum preparation are obtained. It shows a L-arginine deiminase activity of 1,700μ moles/hr/g of microbial cells. Yield of Activity: 64%.
[L-arginine deiminase activity is indicated in terms of micromoles of L-citrullin which are produced by reaction with L-arginine. The reaction with L-arginine is conducted by adding 10 g of the immobilized preparation to an aqueous 0.5 M L-arginine hydrochloride solution (pH 6.0) containing 0.01% of triethanolamine laurylsulfate, and shaking the mixture at 37° C. for one hour. The amount of L-citrullin produced is assayed colorimetrically by using diacetylmonooxim as a coloring agent.]

(2) 20 g of the immobilized *Pseudomonas putidum* preparation obtained in paragragh (1) are packed in a column (1.6 cm in diameter and 12 cm in height). An aqueous 0.5 M L-arginine hydrochloride solution (pH 6.0) is passed through the column at 37° C. at a flow rate of 4.5 or 12 ml/hr. The amount of L-citrullin in the effluent solution is assayed in the same manner as described in paragraph (1), and the percentage conversion of L-arginine into L-citrullin is calculated therefrom. The results are shown in Table 4.

Table 4

| Operation period (days) | Conversion (%) of L-arginine into L-citrullin | |
|---|---|---|
| | 4.5 ml/hr | 12 ml/hr |
| 1 | 100 | 55 |
| 3 | 100 | 55 |
| 6 | 100 | 54 |
| 8 | 100 | 55 |
| 10 | 100 | 54 |
| 13 | 100 | 54 |
| 15 | 100 | 53 |
| 17 | 100 | 51 |
| 20 | 100 | 50 |
| 22 | 100 | 50 |
| 24 | 100 | 47 |
| 27 | 100 | 48 |
| 29 | 100 | 48 |
| 31 | 100 | 46 |

The half-life of the enzymatic activity of the immobilized *Pseudomonas putidum* preparation is about 160 days.

EXAMPLE 22

Microbial cells of *Escherichia coli* ATCC 11303 obtained in the same manner as described in Example 5 are lyophilized. 1.1 g of the lyophilized microbial cells are suspended in 8 ml of an aqueous physiological saline solution. 32 ml of an aqueous 3.2% carrageenan (the trade name "GENU GEL Type WG") solution previously warmed to 40° C. are added to the suspension, and the mixture is added dropwise to an aqueous 2% potassium chloride solution. The resultant gel particles (about 3 mm in diameter) are collected by filtration. 32 g (wet form) of an immobilized *Escherichia coli* preparation are thereby obtained. It shows as aspartase activity of 13,800μ moles/hr. Yield of Activity: 13%

EXAMPLE 23

Microbial cells of *Escherichia coli* ATCC 11303 obtained in the same manner as described in Example 5 are treated with acetone to give acetone powder. 576 mg of the thus obtained acetone powder are suspended in 6 ml of an aqueous physiological saline solution. 24 ml of an aqueous 3.2% carrageenan (the trade name "GENU GEL Type WG") solution previously warmed to 40° C. are added to the suspension, and the mixture is added dropwise to an aqueous 2% potassium chloride solution. The resultant gel particles (about 3 mm in diameter) are collected by filtration. 26.8 g (wet form) of an immobilized *Escherichia coli* preparation are obtained. It shows an aspartase activity of 1,118μ moles/hr/g. Yield of Activity: 39%.

EXAMPLE 24

*Achromobacter liquidum* IAM 1667 is inoculated into 100 ml of an aqueous medium (pH 7.0) containing one % of glucose, 0.2% of dipotassium phosphate, 0.05% of monopotassium phosphate, 0.1% of ammonium chloride, 0.02% of magnesium sulfate 7 hydrate, 0.1% of yeast extract and 0.02% of L-histidine hydrochloride. The medium is cultivated at 30° C. for 24 hours under shaking. Then, the microbial cells are collected by centrifugation. The microbial cells thus obtained are suspended in 4 ml of an aqueous physiological saline solution. The suspension is heated at 70° C. for 30 minutes, and then 16 ml of an aqueous 2.5% carrageenan (the trade name "GENU GEL Type WG") solution previously warmed to 37° C. are added thereto. The mixture is added dropwise to an aqueous 2% potassium chloride solution. The resultant gel particles (about 3 mm in diameter) are collected by filtration. 20 g (wet form) of an immobilized *Achromobacter liquidum* preparation are obtained. It shows a L-histidine ammonia-lyase activity of 434μ moles/hr/g of microbial cells. Yield of Activity: 62%.

[L-histidine ammonia-lyase activity is indicated in terms of micromoles of urocanic acid which are produced by reaction with L-histidine. The reaction with L-histidine is conducted by adding 10 g of the immobilized preparation to 30 ml of an aqueous 0.25 M L-histidine solution (pH 9.0), and shaking the mixture at 37° C. for one hour. The amount of urocanic acid produced in assayed colorimetrically at 277 nm (molecular extinction coefficient = $1.88 \times 10^{-4}$ (pH 7.4)).]

EXAMPLE 25

*Micrococcus ureae* IAM 1010 is inoculated into 400 ml of an aqueous medium (pH 7.0) containing the same ingredients as described in Example 24. The medium is cultivated at 30° C. for 24 hours under shaking. Then, the microbial cells are collected by centrifugation. The cells thus obtained are treated in the same manner as described in Example 20. 20 g (wet form) of an immobilized *Micrococcus ureae* preparation are thereby obtained as gel particles (about 3 mm in diameter). It shows a L-histidine ammonia-lyase activity of 299μ moles/hr/g of microbial cells. Yield of Activity: 59%.

EXAMPLE 26

*Streptomyces griseus* IFO (Institute for Fermentation, Osaka, Japan) 3430 is inoculated into 200 ml of an aqueous medium (pH 7.0) containing one % of peptone, 0.25% of yeast extract, 0.5% of meat extract, one % of D-xylose, 0.05% of magnesium sulfate 7 hydrate, 0.024% of cobaltous chloride 6 hydrate and 0.5% of sodium chloride. The medium is cultivated at 30° C. for 48 hours under shaking. Then, the microbial cells are collected by centrifugation. The microbial cells thus obtained are suspended in 20 ml of an aqueous physiological saline solution, and 80 ml of an aqueous 3.2% carrageenan (the trade name "GENU GEL Type WG") solution previously warmed to 40° C. are added to the suspension under heating (in a water bath, bath temperature: 40° C.). The mixture is added dropwise to an aqueous 2% potassium chloride solution. The resultant gel particles (about 3 mm in diameter) are collected by filtration. 83 g (wet form) of an immobilized *Streptomyces griseus* preparation are obtained. It shows a glucose isomerase activity of 9.2μ moles/hr/g. Yield of Activity: 31%.

EXAMPLE 27

2.5 g of heat-treated microbial cells (glucose isomerase activity: 7,740 units/g) of *Streptomyces phaeochromogenus* are suspended in 5 ml of water. 20 ml of an aqueous 3.1% carrageenan (the trade name "GENU GEL Type WG") solution previously warmed to 40° C. are added to the suspension, and the mixture is added dropwise to an aqueous one % potassium chloride solution. The resultant gel particles (about 3 mm in diameter) are collected by filtration, and then washed with an aqueous one % potassium chloride solution. 22.7 g (wet form) of an immobilized *Streptomyces phaeochromogenus* preparation are obtained. It shows a glucose isomerase activity of 443 units/g.

EXAMPLE 28

(1) *Serratia marcescens* ATCC 21740 (isoleucine hydroxamate- and α-aminobutyric acid-resistant mutant) is inoculated into 100 ml of an aqueous medium (pH 7.0) containing 0.5% of glucose, 1.25% of yeast extract, 1.0% of peptone, 0.5% of meat extract and 0.5% of sodium chloride. The medium is cultivated at 30° C. for 24 hours under shaking. Then, the microbial cells are collected by centrifugation. The microbial cells thus obtained are suspended in an aqueous physiological saline solution. 16 ml of an aqueous 3.2% carrageenan (the trade name "GENU GEL Type WG") solution previously warmed to 37° C. are added to 4 ml of the suspension (microbial cells content: 2 g/4 ml), and the mixture is added dropwise to an aqueous 2% potassium chloride solution. The resultant gel particles (about 3 mm in diameter) are collected by filtration. 20 g (wet form) of an immobilized *Serratia marcescens* preparation are obtained. It shows a L-isoleucine-productivity of 8.6$\mu$ moles/hr/g of microbial cells.

[L-isoleucine-productivity is estimated by adding 5 g of the immobilized preparation to 20 ml of an aqueous solution (pH 7.5) containing 5% of glucose, one % of urea, 2% of DL-threonine, 2% of dipotassium phosphate and 0.05% of magnesium sulfate 7 hydrate, and shaking the mixture at 30° C. for 6 hours. The amount of L-isoleucine produced is bioassayed by using *Leuconostoc mesenterioides* P-60(ATCC 9135).]

(2) 10 g of the immobilized *Serratia marcescens* preparation obtained in paragraph (1) are packed in a column. 50 ml of an aqueous solution (pH 7.5) containing 5% of glucose, one % of urea, 2% of DL-threonine, 2% of dipotassium phosphate and 0.05% of magnesium sulfate 7 hydrate are passed through the column at a flow rate of 250 ml/hr. The effluent is again passed through the column at the same flow rate, and this operation is repeated for 5 hours. 43$\mu$ moles of L-isoleucine are accumulated in the reaction mixture.

EXAMPLE 29

2 g of microbial cells of *Serratia marcescens* Hd-Mhr ATCC 31026 (FERM P. 2120) (L-histidine ammonialyase-lacking and 2-methylhistidine-resistant mutant) are treated in the same manner as described in Example 28-(1). 20 g (wet form) of an immobilized *Serratia marcescens* preparation are obtained. It shows a L-histidine-productivity of 7.2$\mu$ moles/hr/g of microbial cells.

[L-histidine-productivity is estimated by adding 5 g of the immobilized preparation to 20 ml of an aqueous solution (pH 8.0) containing 5% of glucose, 2% of urea, 2% of dipotassium phosphate and 0.2% of magnesium sulfate 7 hydrate, and shaking the mixture at 30° C. for 6 hours. The amount of L-histidine produced is bioassayed by using *Leuconostoc mesenterioides* P-60 (ATCC 9135).]

EXAMPLE 30

2 g of microbial cells of Bacillus subtilis AHr Aur-9 ATCC 31002 (FERM P. 1998) (arginine hydroxamate- and 6-azauracil-resistant mutant) are treated in the same manner as described in Example 28-(1). 20 g (wet form) of an immobilized *Bacillus subtilis* preparation are obtained. It shows a L-arginine-productivity of 21$\mu$ moles/hr/g of microbial cells.

[L-arginine-productivity is estimated by adding 5 g of the immobilized preparation to 20 ml of an aqueous solution (pH 7.5) containing 5% of glucose, 2.5% of ammonium chloride, 2% of sodium L-aspartate, 2% of dipotassium phosphate and 0.0002% of magnesium 7 hydrate, and shaking the mixture at 30° C. for 6 hours. The amount of L-arginine produced is bioassayed by using *Leuconostoc mesenterioides* P-60 (ATCC 9135).]

EXAMPLE 31

One g of microbial cells of *Escherichia coli* ATCC 11303 and 2 g of microbial cells of *Pseudomonas dacunhae* IAM 1152 which are obtained in the same manner as described in Example 5 and 8 are suspended in 3 ml of an aqueous physiological saline solution. 600 mg of carrageenan (the trade name "GENU GEL Type WG") are dissolved in 14.5 ml of water under heating, and the solution is mixed with the microbial cells suspension obtained above. The mixture is added dropwise to an aqueous 2% potassium chloride solution. The resultant gel particles (about 3 mm in diameter) are collected by filtration. 20 g (wet form) of an immobilized microbial cells preparation are obtained. It shows a L-alanine-productivity of 340$\mu$ moles/hr/g of microbial cells. [L-alanine-productivity is estimated by adding 5 g of the immobilized preparation to 30 ml of an aqueous 1 M ammonium fumarate solution (pH 7.0) containing $10^{-4}$ M pyridoxal phosphate, and shaking the mixture at 30° C. for one hour. The amount of L-alanine produced as assayed in the same manner as described in Example 8.]

EXAMPLE 32

(1) *Escherichia coli* ATCC 11303 is inoculated into 500 ml of an aqueous medium (pH 7.0) containing the same ingredients as described in Example 5. The medium is cultivated at 37° C. for 24 hours. Then, the microbial cells are collected by centrifugation. The microbial cells thus obtained are suspended in 16 ml of an aqueous physiological saline solution, and 64 ml of an aqueous 3.2% carrageenan (the trade name "GENU GEL Type WG") solution previously warmed to 40° C. are added to the suspension under heating (in a water bath, bath temperature: 40° C.). The mixture is added dropwise to an aqueous 1 M ammonium fumarate solution (pH 8.5) containing 1 mM magnesium chloride. The resultant gel particles (about 3 mm in diameter) are collected by filtration. 60.4 g (wet form) of an immobilized *Escherichia coli* preparation are obtained. It shows an aspartase activity of 143.4$\mu$ moles/hr/g. Yield of Activity: 84%.

(2) 60.4 g of the immobilized *Escherichia coli* preparation obtained in paragraph (1) are packed in a column (4 cm in diameter and 8 cm in height), and incubated at 37° C. for 48 hours. After incubation, the immobilized preparation shows an aspartase activity of 278, 422$\mu$ moles/hr. Then, 1000 ml of an aqueous 1 M ammonium fumarate solution (pH 8.5) containing 1 mM magnesium chloride are passed through the column at 37° C. at a flow rate of 50 ml/hr. The effluent is adjusted to pH 2.8, and the crystalline precipitates are collected by filtration. 122 g of L-aspartic acid are obtained.

EXAMPLE 33

*Serratia marcescens* OUT (Faculty of Technology, Osaka University, Japan) 8259 is treated in the same manner as described in Example 32-(1). 50.8 g (wet form) of an immobilized *Serratia marcescens* preparation are obtained as gel particles (about 3 mm in diameter). It shows an aspartase activity of 36.9$\mu$ moles/hr/g. Yield of Activity: 87%.

EXAMPLE 34

*Proteus vulgaris* OUT 8226 is treated in the same manner as described in Example 32-(1). 44.0 g (wet form) of an immobilized *Proteus vulgaris* preparation are obtained as gel particles (about 3 mm in diameter). It shows an aspartase activity of 586.9$\mu$ moles/hr/g. Yield of Activity: 100%.

EXAMPLE 35

*Bacterium succinium* IAM 1017 is treated in the same manner as described in Example 32-(1). 54.8 g (wet form) of an immobilized *Bacterium succinium* preparation are obtained as gel particles (about 3 mm in diameter). It shows an aspartase activity of 295.5$\mu$ moles/hr/g. Yield of Activity: 100%.

EXAMPLE 36

*Pseudomonas aeruginosa* OUT 8252 is treated in the same manner as described in Example 32-(1). 39.8 g (wet form) of an immobilized *Pseudomonas aeruginosa* preparation are obtained as gel particles (about 3 mm in diameter). It shows an aspartase activity of 30.1$\mu$ moles/hr/g. Yield of Activity: 87%.

EXAMPLE 37

5 g of heat-treated microbial cells (glucose isomerase activity: 7,740 units/g) of *Streptomyces phaeochromogenus* are suspended in 10 ml of water. 40 ml of an aqueous 3.1% carrageenan (the trade name "GENU GEL Type WG") solution previously warmed to 40° C. are added to the suspension, and the mixture is added dropwise to an aqueous 4% ammonium chloride solution. The resultant gel particles (about 3 mm in diameter) are collected by filtration, and then washed with an aqueous 4% ammonium chloride solution. 57.8% g (wet form) of an immobilized *Streptomyces phaeochromogenus* preparation are obtained. It shows a glucose isomerase activity of 214 units/g.

EXAMPLE 38

2 g of heat-treated microbial cells (glucose isomerase activity: 7,740 units/g) of *Streptomyces phaeochromogenus* are suspended in 4 ml of water. 16 ml of an aqueous 1.5% carrageenan (manufactured by The Kopenhagen Pectin Factory Ltd., under the trade name "GENU VISCO J") solution previously warmed to 40° C. are added to the suspension, and the mixture is added dropwise to an aqueous 0.1 M magnesium chloride solution. The resultant gel particles (about 3 mm in diameter) are collected by filtration. The gel particles are added to a mixture of 10 ml of an aqueous 1 M ammonium chloride solution and 4 ml of an aqueous 25% glutaraldehyde solution, and the mixture is shaken at 30° C. for 60 minutes. Then, the gel particles are collected by filtration. 18.7 g (wet form) of an immobilized *Streptomyces phaeochromogenus* preparation are obtained. It shows a glucose isomerase activity of 141 units/g.

EXAMPLE 39

2 g of heat-treated microbial cells (glucose isomerase activity: 7,740 units/g) of *Streptomyces phaeochromogenus* are suspended in 4 ml of water. 16 ml of an aqueous 1.16% furcellaran (manufactured by Litex Co., Denmark) solution previously warmed to 40° C. are added to the suspension, and the mixture is added dropwise to an aqueous 2% potassium chloride solution. The resultant gel particles (about 3 mm in diameter) are collected by filtration, and then washed with an aqueous 2% potassium chloride solution. 15.3 g (wet form) of an immobilized *Streptomyces phaeochromogenus* preparation are obtained. It shows a glucose isomerase activity of 759 units/g.

EXAMPLE 40

2 g of heat-treated microbial cells (glucose isomerase activity: 7,740 units/g) of *Streptomyces phaeochromogenus* are suspended in 4 ml of water. 16 ml of an aqueous 1.16% furcellaran (manufactured by Litex Co., Denmark) solution previously warmed to 40° C. are added to the suspension, and the mixture is added dropwise to an aqueous 4% ammonium chloride solution. The resultant gel particles (about 3 mm in diameter) are collected by filtration, and then washed with an aqueous 4% ammonium chloride solution. 16.4 g (wet form) of an immobilized *Streptomyces phaeochromogenus* preparation are obtained. It shows a glucose isomerase activity of 444 units/g.

EXAMPLE 41

2 g of heat-treated microbial cells (glucose isomerase activity: 7,740 units/g) of *Streptomyces phaeochromogenus* are suspended in 4 ml of water. 16 ml of an aqueous one % furcellaran (manufactured by Litex Co., Denmark) solution containing 1.25% of gelatin (said furcellaran solution being previously warmed to 40° C.) are added to the suspension, and the mixture is added dropwise to an aqueous 2% potassium chloride solution. The resultant gel particles (about 3 mm in diameter) are collected by filtration, and then washed with an aqueous 2% potassium chloride solution. 16.6 g (wet form) of an immobilized *Streptomyces phaeochromogenus* preparation are obtained. It shows a glucose isomerase activity of 317 units/g.

EXAMPLE 42

2 g of heat-treated microbial cells (glucose isomerase activity: 7,740 units/g) of *Streptomyces phaeochromogenus* are suspended in 4 ml of water. 16 ml of an aqueous one % furcellaran (manufactured by Litex Co., Denmark) solution containing 1.25% of gelatin (said furcellaran solution being previously warmed to 40° C.) are added to the suspension, and the mixture is added dropwise to an aqueous 4% ammonium chloride solution. The resultant gel particles (about 3 mm in diameter) are collected by filtration, and then washed with an aqueous 4% potassium chloride solution. 16.9 g (wet form) of an immobilized *Streptomyces phaeochromogenus* preparation are obtained. It shows a glucose isomerase activity of 421 units/g.

EXAMPLE 43

1.8 g of gel particles (about 3 mm in diameter) obtained in the same manner as described in Example 40 are added to 20 ml of an aqueous 1 M ammonium chloride solution and 0.8 ml of an aqueous 25% glutaraldehyde solution. The mixture is shaken at 30° C. for 60 minutes. The gel particles are collected by filtration, and then washed with ice-water. 1.7 g (wet form) of an immobilized *Streptomyces phaeochromogenus* preparation are obtained. It shows a glucose isomerase activity of 66 units/g.

EXAMPLE 44

(1) 1.66 g of gel particles (about 3 mm in diameter) obtained in the same manner as described in Example 41 are added to a mixture of 0.8 ml of an aqueous 25% glutaraldehyde solution and 20 ml of an aqueous 2% potassium chloride solution. The mixture is shaken at 30° C. for 30 minutes. The gel particles are collected by filtration, and then washed with ice-water. 1.7 g (wet form) of an immobilized *Streptomyces phaeochromogenus* preparation are obtained. It shows a glucose isomerase activity of 318 units/g.

(2) 10 g of the immobilized *Streptomyces phaeochromogenus* preparation obtained in paragraph (1) are packed in a column (1.6 cm in diameter and 14 cm in height). An aqueous 50% glucose solution (pH 7.0) containing 0.01 M magnesium sulfate, 1 mM cobaltous chloride and 0.1 M sodium sulfite is passed through the column at 60° C. The glucose isomerase activity of the immobilized *Streptomyces phaeochromogenus* preparation is assayed at intervals. The results are shown in Table 5. The half-life of the enzymatic activity of the immobilized *Streptomyces phaeochromogenus* preparation is about 180 days. As seen from these data, the immobilized *Streptomyces phaeochromogenus* preparation shows a high enzymatic activity for a long period of time when used for the continuous enzymatic reaction.

Table 5

| Operation period (days) | Glucose isomerase activity (units) | Potency ratio of enzymatic activity* (%) |
|---|---|---|
| 0 | 3,180 | 100 |
| 10 | 3,020 | 95 |
| 21 | 2,961 | 93 |
| 30 | 2,832 | 89 |
| 50 | 2,618 | 82 |
| 71 | 2,422 | 76 |
| 91 | 2,164 | 68 |

Note:
*Potency ratio of enzymatic activity is calculated by the formula shown in the foot-note of Table 1.

EXAMPLE 45

1.69 g of gel particles (about 3 mm in diameter) obtained in the same manner as described in Example 42 are added to a mixture of 2 ml of an aqueous 1 M ammonium chloride solution, 0.8 ml of an aqueous 25% glutaraldehyde solution and 17.2 ml of water. The mixture is shaken at 30° C. for 30 minutes. The gel particles are collected by filtration, and then washed with ice-water. 1.7 g (wet form) of an immobilized *Streptomyces phaeochromogenus* preparation are obtained. It shows a glucose isomerase activity of 192 units/g.

EXAMPLE 46

Microbial cells of *Escherichia coli* ATCC 11303 obtained in the same manner as described in Example 5 are suspended in 8 ml of water. 64 ml of an aqueous 3.2% carrageenan (the trade name "GENU GEL Type WG") solution previously warmed to 40° C. are added to the suspension, and the mixture is added dropwise to acetone (cooled to $-1°$ to 0° C.). After dropwise addition, the mixture is stirred for 10 minutes. The resultant gel particles (about 3 mm in diameter) are collected by filtration, and then washed with an aqueous 4% ammonium chloride solution. 54.0 g (wet form) of an immobilized *Escherichia coli* preparation are obtained. It shows an aspartase activity of $3,441\mu$ moles/hr/g. Yield of Activity: 345%.

EXAMPLE 47

5 g of heat-treated microbial cells (glucose isomerase activity: 7,740 units/g) of *Streptomyces phaeochromogenus* are suspended in 10 ml of water. 40 ml of an aqueous 3% sodium salt of cellulose sulfate (manufactured by KELCO Co., under the trade name "KELCO SCS") solution previously warmed to 37° C. are added to the suspension, and the mixture is added dropwise to an aqueous 2% potassium chloride solution. The resultant gel particles (about 3 mm in diameter) are collected by filtration, and then washed with an aqueous 2% potassium chloride solution. 48 g (wet form) of an immobilized *Streptomyces phaeochromogenus* preparation are obtained. It shows a glucose isomerase activity of 443 units/g.

EXAMPLE 48

(1) 8 g of microbial cells of *Escherichia coli* ATCC 11303 obtained in the same manner as described in Example 5 are suspended in 5 ml of a physiological saline solution. 80 ml of an aqueous 2.2% carrageenan (the trade name "GENU GEL Type WG" solution containing one % of locust been gum (said carrageenan solution being previously warmed to 40° C.) are mixed with the suspension. 250 ml of an aqueous potassium chloride solution are added gradually to the mixture, and said mixture is allowed to stand at 4° C. for 30 minutes. The resultant gel is cut into cubes of 3 mm in each side, and then washed with an aqueous 2% potassium chloride solution. 89.3 g of the gel cubes thus obtained are immersed in 100 ml of ice-cold ethanol, and glutaraldehyde is added thereto until the final concentration thereof becomes 0.49%. The mixture is allowed to stand for 15 minutes under ice-cooling. Then, the gel cubes are collected by filtration, and then washed with an aqueous 2% potassium chloride solution. 86.2 g (wet form) of an immobilized *Escherichia coli* preparation are obtained. It shows an aspartase activity of $32,183\mu$ moles/hr/g of microbial cells.

(2) 11.1 g of the immobilized *Escherichia coli* preparation obtained in paragraph (1) are packed in a column (1.6 cm in diameter and 12 cm in height). An aqueous 1 M ammonium fumarate solution (pH 8.5) containing 1 mM of magnesium chloride is passed through the column at 37° C. at a flow rate of 6 ml/hr. The enzymatic activity of the immobilized *Escherichia coli* preparation is assayed at intervals. The results are shown in Table 6. The half-life of the enzymatic activity of the immobilized *Escherichia coli* preparation is about 113 days. As seen from these data, the immobilized preparation shows a high enzymatic activity for a long period of time when used for the continuous enzymatic reaction.

Table 6

| Operation period (days) | Aspartase activity (μ moles/hr/g of cells) | Potency ratio of enzymatic activity* (%) |
|---|---|---|
| 0 | 32,183 | 100 |
| 6 | 31,413 | 98 |
| 8 | 31,625 | 98 |
| 12 | 31,600 | 98 |
| 19 | 31,906 | 99 |
| 22 | 31,036 | 96 |
| 29 | 30,574 | 95 |
| 40 | 29,932 | 93 |

Note:
*Potency ratio of enzymatic activity is calculated by the formula shown in the foot-note of Table 1.

EXAMPLE 49

(1) *Pseudomonas dacuhae* IAM 1152 is inoculated into 120 ml of an aqueous medium (pH 7.0) containing 1.4% of sodium glutamate, 0.2% of casamino acid, 0.9% of peptone, 0.05% of monopotassium phosphate and 0.01% of magnesium sulfate 7 hydrate. The medium is cultivated at 30° C. for 24 hours under shaking. Then, the microbial cells are collected by centrifugation. 2 g of the microbial cells are suspended in 5 ml of a physiological saline solution. On the other hand, 600 mg of carrageenan (the trade name "GENU GEL Type WG") are dissolved in 15 ml of water. The carrageenan solution is mixed with the suspension at 37° C., and one ml of an aqueous 1 M hexamethylenediamine solution (pH 7.0) is added thereto. The mixture is allowed to stand at 4° C. for 30 minutes. The resultant gel is cut into cubes of 4 mm in each side. The gel cubes are added to 50 ml of an aqueous 2% ammonium chloride solution containing one % of glutaraldehyde, and the mixture is allowed to stand at 0° C. for 15 minutes. Then, the gel cubes are collected by filtration, and washed with an aqueous 1% ammonium chloride solution. 22 g (wet form) of an immobilized *Pseudomonas dacuhae* preparation are obtained. It shows an aspartate β-decarboxylase activity of 3,567μ moles/hr/g of microbial cells.

(2) 22 g of the immobilized *Pseudomonas dacuhae* preparation obtained in paragraph (1) are packed in a column (1.6 cm in diameter and 10.5 cm in height). An aqueous 1 M ammonium asparaginate solution (pH 5.5) containing $10^{-4}$ M of pyridoxal phosphate is passed through the column upward from the bottom at 37° C. at a flow rate of 13.8 ml/hr. The amount of L-alanine in the effluent solution is bioassayed by using Leuconostoc citrovorum ATCC 8081. The results are shown in Table 7. The half-life of the enzymatic activity of the immobilized *Pseudomonas dacuhae* preparation is about 159 days. As seen from these data, the immobilized preparation shows a high enzymatic activity for a long period of time when used for the continuous enzymatic reaction.

Table 7

| Operation period (days) | Aspartate β-decarboxylase activity (μmoles/ml) | Potency ratio of enzymatic activity* (%) |
|---|---|---|
| 1 | 517 | 100 |
| 3 | 556 | 108 |
| 4 | 528 | 102 |
| 5 | 576 | 111 |
| 7 | 538 | 104 |
| 12 | 528 | 102 |
| 14 | 528 | 102 |
| 20 | 528 | 102 |
| 24 | 521 | 101 |
| 26 | 489 | 95 |
| 45 | 450 | 87 |

EXAMPLE 50

(1) *Brevibacterium flavum* ATCC 14067 is inoculated into 500 ml of an aqueous medium (pH 7.0) containing 2.0% of corn steep liquor, 2.0% of malonic acid, 0.2% of diammonium citrate, 0.2% of monopotassium phosphate and 0.05% of magnesium sulfate 7 hydrate. The medium is cultivated at 30° C. for 48 hours under shaking. Then, the microbial cells are collected by centrifugation. 8.0 g of the microbial cells are suspended in 8 ml of a physiological saline solution. 34 ml of an aqueous 5.0% carrageenan (the trade name "GENU GEL Type WG") solution previously warmed to 50° C. are mixed with the suspension. 250 ml of an aqueous 2% potassium chloride solution are added gradually to the mixture, and said mixture is allowed to stand at 4° C. for 5 hours. The resultant gel is cut into cubes of 3 mm in each side. The gel cubes are washed with an aqueous 2% potassium chloride solution. 49.9 g (wet form) of an immobilized *Brevibacterium flavum* preparation are obtained. It shows a fumarase activity of 503μ moles/hr/g of microbial cells.

(2) 6.3 g of the immobilized *Brevibacterium flavum* preparation obtained in paragraph (1) are packed in a column (1.6 cm in diameter and 12 cm in height). An aqueous 1 M potassium fumarate solution (pH 7.0) is passed through the column at 37° C. at a flow rate of 6 ml/hr. The enzymatic activity of the immobilized *Brevibacterium flavum* preparation is assayed at intervals. The results are shown in Table 8. The half-life of the immobilized *Brevibacterium flavum* preparation is about 69 days. As seen from this data, the immobilized preparation shows a high enzymatic activity for a long period of time when used for the continuous enzymatic reaction.

Table 8

| Operation period (days) | Fumarase activity (μ moles/ml) | Potency ratio of enzymatic activity* (%) |
|---|---|---|
| 1 | 1,768 | 100 |
| 2 | 1,767 | 100 |
| 4 | 1,472 | 83 |
| 9 | 1,422 | 80 |
| 13 | 1,401 | 79 |
| 18 | 1,374 | 78 |
| 20 | 1,355 | 77 |
| 25 | 1,307 | 74 |
| 30 | 1,308 | 74 |

Note:
*Potency ratio of enzymatic activity is calculated by the formula shown in the foot-note of Table 1.

What we claim is:

1. An immobilized catalytically active substance which comprises a catalytically active enzyme or microorganism or a water-insoluble, hydrophilic, catalytically active carrier-bound enzyme or microorganism entrapped within the gel matrix of a sulfated polysaccharide (sulfate moiety content in the molecule: more than 10 w/w %) containing therein ammonium ion, a metal ion having an atomic weight greater than 24, a water-soluble organic amine or a water-miscible organic solvent.

2. The immobilized catalytically active substance of claim 1, wherein said sulfated polysaccharide contains between about 12 and 62 w/w % of sulfate moiety in its molecule.

3. The immobilized catalytically active substance of claim 2, wherein said sulfated polysaccharide is carrageenan, furcellaran or a cellulose sulfate (sulfate moiety content: between about 12 and 62 w/w %).

4. The immobilized catalytically active substance of claim 2, wherein said sulfated polysaccharide is kappa-carrageenan, iota-carrageenan or furcellaran.

5. The immobilized catalytically active substance of claim 1, wherein the gel matrix of the sulfated polysaccharide contains $10^{-1}$ to $10^4$ millimoles (per gram of the sulfated polysaccharide) of said ion, amine or solvent.

6. The immobilized catalytically active substance of claim 1, wherein said metal ion is selected from an alkali metal ion (the alkali metal ion belonging to a group not lower than Series 4 in Mendeleev's Periodic Table), an alkali earth metal ion, aluminium ion, lead ion, manganese ion, ferric ion and ferrous ion, said amine is selected from an alkylenediamine of one to 20 carbon atoms, a phenylenediamine, a hydroxamate, hydrazide, alkyl ester or amide of a basic amino acid, a S-aminoalkyl-cysteine, an aminoalkylguanidine, δ-hydroxy-lysine, histamine and serotonine, and said organic solvent is selected from an alkanone of 3 to 5 carbon atoms, an alkanol of one to 3 carbon atoms, dioxane, tetrahydrofuran, dimethylformamide, dimethylsulfoxide, ethyleneglycol and glycerin.

7. The immobilized catalytically active substance of claim 6, wherein the gel matrix of the sulfated polysaccharide contains between about $10^{-1}$ and $10^4$ millimoles (per gram of the sulfated polysaccharide) of said ion, amine or solvent.

8. The immobilized catalytically active substance of claim 1, wherein the gel matrix of the sulfated polysaccharide contains ammonium ion, potassium ion, magnesium ion, calcium ion, strontium ion, barium ion, an alkylenediamine of one to 20 carbon atoms, a phenylenediamine, an alkanone of 3 to 5 carbon atoms or an alkanol of one to 3 carbon atoms.

9. The immobilized catalytically active substance of claim 8, wherein the gel matrix contains between $10^{-1}$ and $10^4$ millimoles (per gram of the sulfated polysaccharide) of said ion, amine or solvent.

10. The immobilized catalytically active substance of claim 6, wherein said alkali metal ion is potassium ion, said alkali earth metal ion is magnesium, calcium, strontium or barium ion, said phenylenediamine is p-phenylenediamine, m-phenylenediamine or o-phenylenediamine, said hydroxamate, hydrazide, alkyl ester or amide of the basic amino acid is lysine hydroxamate, histidine hydroxamate, tryptophan hydroxamate, lysine hydrazide, histidine hydrazide, lysine methyl ester, histidine methyl ester or lysine amide, said S-aminoalkylcysteine is S-(2-aminoethyl)-cysteine, and said aminoalkylguanidine is agmatine.

11. The immobilized catalytically active substance of claim 2, wherein the gel matrix of the sulfated polysaccharide contains between about $10^{-1}$ and $10^4$ millimoles (per gram of sulfated polysaccharide) of said ion, amine or solvent.

12. The immobilized catalytically active substance of claim 11, wherein the ion is selected from ammonium ion, an alkali metal ion (said alkali metal ion belonging to a group not lower than Series 4 in Mendeleev's Periodic Table), an alkali earth metal ion, aluminium ion, lead ion, manganese ion, ferric ion and ferrous ion, said amine is selected from an alkylenediamine of one to 20 carbon atoms, a phenylenediamine, a hydroxamate, hydrazide, alkyl ester or amide of a basic amino acid, a S-aminoalkyl-cysteine, an aminoalkylguanidine, δ-hydroxy-lysine, histamine and serotonine, and said organic solvent is selected from an alkanone of 3 to 5 carbon atoms, an alkanol of one to 3 carbon atoms, dioxane, tetrahydrofuran, dimethylformamide, dimethylsulfoxide, ethyleneglycol and glycerin.

13. The immobilized catalytically active substance of claim 12, wherein said alkali metal ion is potassium ion, said alkali earth metal ion is magnesium, calcium, strontium or barium ion, said phenylenediamine is p-phenylenediamine, m-phenylenediamine or o-phenylenediamine, said hydroxyamate, hydrazide, alkyl ester or amide of the basic amino acid is lysine hydroxamate, histidine hydroxamate, tryptophan hydroxamate, lysine hydrazide, histidine hydrazide, lysine methyl ester, histidine methyl ester or lysine amide, said S-aminoalkylcysteine is S-(2-aminoethyl)-cysteine and said aminoalkyl guanidine is agmatine.

14. The immobilized catalytically active substance of claim 3, wherein the gel matrix of the sulfated polysaccharide contains between about $10^{-1}$ and $10^4$ millimoles (per gram of the sulfated polysaccharide) of ammonium ion, potassium ion, magnesium ion, calcium ion, strontium ion, barium ion, aluminium ion, lead ion, manganese ion, ferric ion, ferrous ion, an alkylenediamine of one to 20 carbon atoms, p-phenylenediamine, m-phenylenediamine, o-phenylenediamine, lysine hydroxamate, histidine hydroxamate, tryptophan hydroxamate, lysine hydrazide, histidine hydrazide, lysine methyl ester, histidine methyl ester, lysine amide, S-(2-aminoethyl)-cysteine, agmatine, δ-hydroxy-lysine, histamine, serotonine, an alkanone of 3 to 5 carbon atoms, an alkanol of one to 3 carbon atoms, dioxane, tetrahydrofuran, dimethylformamide, dimethylsulfoxide, ethyleneglycol or glycerin.

15. The immobilized catalytically active substance of claim 4, wherein the gel matrix of the sulfated polysaccharide contains between about $10^{-1}$ and $10^4$ millimoles (per gram of the sulfated polysaccharide) of ammonium ion, potassium ion, magnesium ion, an alkylenediamine of one to 20 carbon atoms, an alkanone of 3 to 5 carbon atoms or an alkanol of one to 3 carbon atoms.

16. The immobilized catalytically active substance of claim 1 comprising the catalytically active enzyme or microorganism entrapped within the gel matrix of the sulfated polysaccharide containing the ion, amine or solvent.

17. The immobilized catalytically active substance of claim 2 comprising the catalytically active enzyme or microorganism entrapped within the gel matrix of the sulfated polysaccharide containing the ion, amine or solvent.

18. The immobilized catalytically active substance of claim 5 comprising the catalytically active enzyme or microorganism entrapped within the gel matrix of the sulfated polysaccharide containing the ion, amine or solvent.

19. The immobilized catalytically active substance of claim 12 comprising the catalytically active enzyme or microorganism entrapped within the gel matrix of the sulfated polysaccharide containing the ion, amine or solvent.

20. The immobilized catalytically active substance of claim 15 comprising the catalytically active enzyme or microorganism entrapped within the gel matrix of the sulfated polysaccharide containing the ion, amine or solvent.

21. A method of preparing an immobilized catalytically active substance which comprises the steps of mixing a catalytically active enzyme or microorganism or a water-insoluble, hydrophilic, catalytically active carrier-bound enzyme or microorganism with an aqueous solution of a sulfated polysaccharide (said sulfated polysaccharide containing more than 10 w/w % of sulfate moiety in its molecule), and then contacting the aqueous mixture with ammonium ion, a metal ion having an atomic weight greater than 24, a water-soluble organic amine or a water-miscible organic solvent to give the gel matrix of the sulfated polysaccharide having the enzyme or microorganism or carrier-bound enzyme or microorganism entrapped therein.

22. The method according to claim 21, wherein said sulfated polysaccharide contains between about 12 and 62 w/w % of sulfate moiety in its molecule.

23. The method according to claim 21, wherein said sulfated polysaccharide is carrageenan, furcellaran or a cellulose sulfate (sulfate moiety content: between about 12 and 62 w/w %).

24. The method according to claim 21, wherein said sulfated polysaccharide is kappa-carrageenan, iota-carrageenan or furcellaran.

25. The method according to claim 21, wherein the enzyme or microorganism or carrier-bound enzyme or microorganism is mixed with an aqueous solution containing between about 0.05 and 20 w/w % of the sulfated polysaccharide, and the aqueous mixture is contacted with the solvent or an aqueous solution containing at least 0.1 mM of the ion or amine.

26. The method according to claim 21, wherein the mixing step is carried out at a temperature of between about 30° and 70° C. and at a pH of between about 1 and 13, and the subsequent contacting step is carried out at a temperature of between about −5° and 70° C.

27. The method according to claim 21, wherein the mixing step is carried out at a temperature of between about 30° and 70° C. at a pH of 4 to 10, and the subsequent contacting step is carried out at a temperature of between about −5° and 70° C.

28. The method according to claim 21, wherein said metal ion is selected from an alkali metal ion (the alkali metal ion belonging to a group not lower than Series 4 in Mendeleev's Periodic Table), an alkali earth metal ion, aluminium ion, lead ion, manganese ion, ferric ion and ferrous ion, said organic amine is selected from an alkylenediamine of one to 20 carbon atoms, a phenylenediamine, a hydroxamate, hydrazide, alkyl ester or amide of a basic amino acid, a S-aminoalkyl-cysteine, an aminoalkylguanidine, δ-hydroxy-lysine, histamine and serotonine, and said organic solvent is selected from an alkanone of 3 to 5 carbon atoms, an alkanol of one to 3 carbon atoms, dioxane, tetrahydrofuran, dimethylformamide, dimethylsulfoxide, ethyleneglycol and glycerin.

29. The method according to claim 28, wherein said alkali metal ion is potassium ion, said alkali earth metal ion is magnesium, calcium, strontium or barium ion, said phenylenediamine is p-phenylenediamine, m-phenylenediamine or o-phenylenediamine, said hydroxamate, hydrazide, alkyl ester or amide of the basic amino acid is lysine hydroxamate, histidine hydroxamate, tryptophan hydroxamate, lysine hydrazide, histidine hydrazide, lysine methyl ester, histidine methyl ester or lysine amide, said S-aminoalkyl-cysteine is S-(2-aminoethyl)-cysteine, and said aminoalkylguanidine is agmatine.

30. The method according to claim 21, wherein the enzyme or microorganism or carrier-bound enzyme or microorganism is mixed with an aqueous solution containing between about 0.05 and 20 w/w % of the sulfated polysaccharide, and the aqueous mixture is contacted with an aqueous solution containing at least 0.1 mM of ammonium ion, potassium ion, magnesium ion, calcium ion, strontium ion, barium ion, an alkylenediamine of one to 20 carbon atoms or a phenylenediamine.

31. The method according to claim 21, wherein said sulfated polysaccharide contains between about 12 and 62 w/w % of sulfated moiety in its molecule, the enzyme or microorganism or carrier-bound enzyme or microorganism is mixed with an aqueous solution containing between about 0.05 and 20 w/w % of said sulfated polysaccharide, and the aqueous mixture is contacted with the solvent or an aqueous solution containing at least 0.1 mM of the ion or amine.

32. The method according to claim 31, wherein the ion is selected from ammonium ion, an alkali metal ion (the alkali metal ion belonging to a group not lower than Series 4 in Mendeleev's Periodic Table), an alkali earth metal ion, aluminium ion, lead ion, manganese ion, ferric ion and ferrous ion, the amine is selected from an alkylenediamine of one to 20 carbon atoms, a phenylenediamine, a hydroxamate, hydrazide, alkyl ester or amide of a basic amino acid, a S-aminoalkyl-cysteine, an aminoalkylguanidine, δ-hydroxy-lysine, histamine and serotonine, and the solvent is selected from an alkanone of 3 to 5 carbon atoms, an alkanol of one to 3 carbon atoms, dioxane, tetrahydrofuran, dimethylformamide, dimethylsulfoxide, ethyleneglycol and glycerin.

33. The method according to claim 32, wherein said alkali metal ion is potassium ion, said alkali earth metal ion is magnesium, calcium, strontium or barium ion, said phenylenediamine is p-phenylenediamine, m-phenylenediamine or o-phenylenediamine, said hydroxamate, hydrazide, alkyl ester or amide of the basic amino acid is lysine hydroxamate, histidine hydroxamate, tryptophan hydroxamate, lysine hydrazide, histidine hydrazide, lysine methyl ester, histidine methyl ester or lysine amide, said S-aminoalkyl-cysteine is S-(2-aminoethyl)-cysteine, and said aminoalkylguanidine is agmatine.

34. The method according to claim 21, wherein the sulfated polysaccharide contains between about 12 and 62 w/w % of sulfate moiety in its molecule, the enzyme or microorganism or carrier-bound enzyme or microorganism is mixed at a temperature of between about 30° and 70° C. at a pH of between about 4 and 10 with an aqueous solution containing between about 0.05 and 20 w/w % of said sulfated polysaccharide, and the aqueous mixture is contacted at a temperature of between about −5° and 30° C. with the organic solvent or at a temperature of between 0° and 55° C. with an aqueous solution containing at least 0.1 mM of the ion or amine.

35. The method according to claim 34, wherein the ion is selected from ammonium ion, an alkali metal ion (the alkali metal ion belonging to a group not lower than Series 4 in Mendeleev's Periodic Table), an alkali earth metal ion, aluminium ion, lead ion, manganese ion, ferric ion and ferrous ion, the amine is selected from an alkylenediamine of one to 20 carbon atoms, a phenylenediamine, a hydroxamate, hydrazide, alkyl ester or amide of a basic amino acid, a S-aminoalkylcysteine, an aminoalkylguanidine, δ-hydroxy-lysine, histamine and serotonine, and the solvent is selected from an alkanone of 3 to 5 carbon atoms, an alkanol of one to 3 carbon atoms, dioxane, tetrahydrofuran, dimethylformamide, dimethylsulfoxide, ethyleneglycol and glycerin.

36. The method according to claim 35, wherein said alkali metal ion is potassium ion, said alkali earth metal ion is magnesium, calcium, strontium or barium ion, said phenylenediamine is p-phenylenediamine, m-phenylenediamine or o-phenylenediamine, said hydroxamate, hydrazide, alkyl ester or amide of the basic amino acid is lysine hydroxamate, histidine hydroxamate, tryptophan hydroxamate, lysine hydrazide, histidine hydrazide, lysine methyl ester, histidine methyl ester or lysine amide, said S-aminoalkyl-cysteine is S-(2-aminoethyl)-cysteine, and said aminoalkylguanidine is agmatine.

37. The method according to claim 21, wherein the enzyme or microorganism or carrier-bound enzyme or microorganism is mixed with an aqueous solution of carrageenan, furcellaran or a cellulose sulfate (sulfate moiety content: 12 to 62 w/w %), and the aqueous mixture is contacted with the solvent selected from an alkanone of 3 to 5 carbon atoms, an alkanol of one to 3 carbon atoms, dioxane, tetrahydrofuran, dimethylformamide, dimethylsulfoxide, ethyleneglycol and glycerin, or an aqueous solution containing at least 0.1 mM of the ion or amine selected from ammonium ion, potassium ion, magnesium ion, calcium ion, strontium ion, barium ion, aluminium ion, lead ion, manganese ion, ferric ion, ferrous ion, an alkylenediamine of one to 20 carbon atoms, p-phenylenediamine, m-phenylenediamine, o-phenylenediamine, lysine hydroxamate, histidine hydroxamate, tryptophan hydroxamate, lysine hydrazide, histidine hydrazide, lysine methyl ester, histidine methyl ester, lysine amide, S-(2-aminoethyl)-cysteine, agmatine, $\delta$-hydroxy-lysine, histamine and serotonine.

38. The method according to claim 37, wherein the mixing step is carried out at a temperature of between about 30° and 70° C. and at a pH of 4 to 10, and the subsequent contacing step is carried out at a temperature of between about $-5°$ and 70° C.

39. The method according to claim 21, wherein the enzyme or microorganism or carrier-bound enzyme or microorganism is mixed with an aqueous solution of kappa-carrageenan, iota-carrageenan or furcellaran at a temperature of between about 30° and 70° C. at a pH of between about 4 and 10, and the aqueous mixture is contacted at a temperature of between about $-5°$ and 30° C. with the solvent or at a temperature of between about 0° and 55° C. with an aqueous solution containing at least 0.1 mM of the ion or amine.

40. The method according to claim 39, wherein the ion is ammonium ion, potassium ion or magnesium ion, the amine is an alkylenediamine of one to 20 carbon atoms, and the solvent is an alkanone of 3 to 5 carbon atoms or an alkanol of one to 3 carbon atoms.

41. The method according to claim 21, further including the step of contacing the gel matrix with a gel-hardening agent.

42. The method according to claim 41, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

43. The method according to claim 22, further including the step of contacting the gel matrix with a gel-hardening agent.

44. The method according to claim 43, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

45. The method according to claim 27, further including the step of contacting the gel matrix with a gel-hardening agent.

46. The method according to claim 45, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

47. The method according to claim 28, further including the step of contacting the gel matrix with a gel-hardening agent.

48. The method according to claim 47, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

49. The method according to claim 30, further including the step of contacting the gel matrix with a gel-hardening agent.

50. The method according to claim 49, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and a aliphatic dialdehyde of 3 to 5 carbon atoms.

51. The method according to claim 39, further including the step of contacting the gel matrix with a gel-hardening agent.

52. The method according to claim 51, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

53. The method according to claim 34, further including the step of contacting the gel matrix with a gel-hardening agent.

54. The method according to claim 53, wherein the gel-hardening agent is selected from an aliphatic dialdehyde of 3 to 5 carbon atoms, tannins, dihydroxyacetone, epichlorohydrin, ethyl chloroformate, hexamethylene diisocyanate, toluene diisocyanate, hexamethylene diisothiocyanate, a carbodiimide, a Woodward reagent, and a mixture of ammonia or an alkylenediamine of one to 20 carbon atoms and an aliphatic dialdehyde of 3 to 5 carbon atoms.

55. The method according to claim 46, wherein the gel-hardening agent is employed at a concentration of between about 0.01 and one gram per ml.

56. The method according to claim 54, wherein the gel-hardening agent is employed at a concentration of between about 0.01 and one gram per ml, and the step is carried out at a temperature of between about 0° and 50° C.

57. The method according to claim 53, wherein the gel-hardening agent is an aliphatic dialdehyde of 3 to 5 carbon atoms or a mixture of ammonia or an alkylenediamine of one to 20 carbon atoms and an aliphatic dialdehyde of 3 to 5 carbon atoms.

58. The method according to claim 51, wherein the gel-hardening agent is an aliphatic dialdehyde of 3 to 5 carbon atoms or a mixture of ammonia or an alkylenediamine of one to 20 carbon atoms and an aliphatic dialdehyde of 3 to 5 carbon atoms, and said gel-hardening agent is employed at a concentration of between about 0.01 and one gram per ml, and the step is carried out at a temperature of between about 0° and 50° C.

59. The method according to claim 21, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

60. The method according to claim 22, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

61. The method according to claim 28, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

62. The method according to claim 39, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

63. The method according to claim 41, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

64. The method according to claim 51, further including the step of subjecting the resultant immobilized catalytically active substance to an enzymatic reaction thereof in the presence of ammonium ion, a metal ion having an atomic weight greater than 24, a water-soluble organic amine or a water-miscible organic solvent.

* * * * *